US006511851B1

United States Patent
Payne et al.

(10) Patent No.: US 6,511,851 B1
(45) Date of Patent: Jan. 28, 2003

(54) IDENTIFYING CHANGES IN COMPOSITION OF LIQUIDS

(75) Inventors: Peter Alfred Payne, Knutsford (GB); Richard Mark Dowdeswell, Davenham (GB); Mohammed El Hassan Amrani, Brunswick (GB)

(73) Assignee: Kaiku Limited, Manchester (GB)

(*) Notice: Subject to any disclaimer, the term of this patent is extended or adjusted under 35 U.S.C. 154(b) by 0 days.

(21) Appl. No.: 09/403,237

(22) PCT Filed: Apr. 16, 1998

(86) PCT No.: PCT/GB98/01118

§ 371 (c)(1),
(2), (4) Date: Jan. 3, 2000

(87) PCT Pub. No.: WO98/46985

PCT Pub. Date: Oct. 22, 1998

(30) Foreign Application Priority Data

| Apr. 16, 1997 | (GB) | ............................................. 9707709 |
| Oct. 25, 1997 | (GB) | ............................................. 9722502 |
| Oct. 30, 1997 | (GB) | ............................................. 9722821 |

(51) Int. Cl.[7] ............................................. G01N 27/416
(52) U.S. Cl. ........................ 436/151; 436/149; 436/150
(58) Field of Search ...................... 422/68.1, 76, 82.01, 422/82.02; 435/4, 29; 436/149, 150, 151; 324/204, 441, 442, 615, 663

(56) References Cited

U.S. PATENT DOCUMENTS

| 3,966,973 A | * | 6/1976 | Henry et al. | .................. 426/231 |
| 4,010,715 A | * | 3/1977 | Robar et al. | ............. 119/14.14 |
| 4,160,205 A | * | 7/1979 | Hobbs | ......................... 324/692 |

(List continued on next page.)

FOREIGN PATENT DOCUMENTS

| DE | 1039628 | 9/1958 |
| EP | 036274 | 9/1981 |
| EP | 7211103 | 7/1996 |
| WO | 9207251 | 4/1992 |
| WO | 9318395 | 9/1993 |

OTHER PUBLICATIONS

Amrani et al. "High-frequency measurements of conducting polymers: development of a new technique for sensing volatile chemicals", Meas. Sci. Technol., 1995, v. 6, pp.. 1500–1507.*
Hilland, Jannicke, (1997) Meas. Sci. Technol. 8;901–910.
Perl, et al., (1985) Journal of Colloid and Interface Science 108(2): 528–540.
U.S. 5119034 Jun. 1992.

*Primary Examiner*—Jill Warden
*Assistant Examiner*—Yelena Gakh
(74) *Attorney, Agent, or Firm*—Banner & Witcoff, Ltd.

(57) ABSTRACT

A method for identifying a change in the composition of a liquid, comprising the steps of applying a time varying electrical or electromagnetic input signal to the liquid in a range of frequencies encompassing a resonant frequency of an electrical circuit comprising the liquid; measuring an impedance quantity of the electrical circuit comprising the liquid by means of the output signal as a function of the frequency of the time varying electrical or resonant frequency input signal in said range of frequencies; determining a resonant frequency of the electrical circuit comprising the liquid; after a change in the composition of the liquid, measuring variation in the impedance quantity at or near to the previously determined resonant frequency of the electrical circuit comprising the liquid; and relating the variation in the impedance quantity at or near to the resonant frequency of the electrical circuit comprising the liquid to a change in the composition of the liquid.

40 Claims, 24 Drawing Sheets

U.S. PATENT DOCUMENTS

| | | | |
|---|---|---|---|
| 4,646,070 A | * 2/1987 | Yasuhara et al. | 324/442 |
| 4,701,713 A | * 10/1987 | Eaton et al. | 324/442 |
| 4,810,963 A | * 3/1989 | Blake-Coleman | 324/204 |
| 4,831,324 A | * 5/1989 | Asakura et al. | 324/615 |
| 4,853,638 A | * 8/1989 | Endou et al. | 324/441 |
| 4,869,016 A | * 9/1989 | Diprose et al. | 43/124 |
| 4,885,529 A | * 12/1989 | Lee et al. | 324/663 |
| 4,887,455 A | * 12/1989 | Payne et al. | 73/24.06 |
| 5,003,267 A | 3/1991 | Coleman | |
| 5,177,994 A | * 1/1993 | Moriizumi et al. | 73/23.34 |
| 5,260,665 A | 11/1993 | Goldberg et al. | |
| 5,514,337 A | * 5/1996 | Groger et al. | 422/82.08 |
| 5,725,754 A | * 3/1998 | Belford | 205/789 |
| 5,756,279 A | * 5/1998 | Ebersole et al. | 435/4 |
| 6,028,433 A | * 2/2000 | Cheiky-Zelina et al. | 324/663 |

* cited by examiner

IDENTIFYING CHANGES IN COMPOSITION OF LIQUIDS

This invention relates to methods and apparatus for the assessment of the composition of a liquid, in particular to the detection of impurities present in a liquid, with particular, but by no means exclusive, reference to the detection of impurities present in samples of water.

There is an unfulfilled need for accurate, sensitive and reliable monitoring of water quality. Preferably, a single technique would exhibit wide ranging sensitivity, permitting the detection of a range of pollution types. A variety of substances can cause pollution, including oil, sewage, organic wastes as well as a multitude of industrial by-products. When the water being monitored is a flowing source, such as a river, industrial effluent, sewage flow, tap water or groundwater source, the technique employed is preferably an on-line one. The present invention is primarily—although not exclusively—directed towards on-line monitoring of such flowing sources.

Techniques which have been employed for these purposes include: the inhibition of bacteria, the use of fish, changes in acoustic impedance, optical monitoring, and measurement of biological oxygen demand (BOD), chemical oxygen demand (COD), pH, turbidity and conductivity. The latter technique, that of conductivity measurement, is of the greatest pertinence to the present invention. Such measurements have been used for a number of years to determine water quality, and involve the measurement of the conductance of a water sample when a direct current (dc) electrical signal is applied thereto. The conductance of the water sample is dependent upon the chemical species contained in the sample, and therefore the measured value of the conductance can be taken as an indication of the degree of pollution. However, the technique only provides a single experimental quantity—the dc conductance—and thus the amount of information provided by the technique, concerning the identity and concentration of any pollutants, is limited. Furthermore, correlating variations in conductivity with the presence of pollutants is not an easy matter, since conductivity variations can be caused by normally occurring, natural variations in the composition of the water sample. Such compositional variations can occur over a time scale of minutes, as well as having seasonal causes.

The present invention alleviates the aforementioned problems. For the avoidance of doubt, it is noted that the invention is applicable inter alia to the detection of a wide range of impurities in liquids, including samples of water—flowing and still—emanating from numerous sources, and also including non-conductive liquids, such as oils.

According to a first aspect of the invention there is provided a method for assessing the composition of a liquid comprising the steps of:
 applying an electrical or electromagnetic signal to the liquid; and
 measuring an impedance quantity at, or near to, the resonant frequency of the liquid or an electrical circuit comprising the liquid so that the resonant frequency or variations in the resonant frequency, can be detected.

The impedance quantity may be measured as a function of the frequency of an applied electrical signal.

A time varying electrical signal may be applied to the liquid.

The time varying electrode signal may be an ac signal and the frequency of the ac signal may be varied.

Alternatively, the measurement of an impedance quantity may comprise a time to frequency domain transformation of the time varying electrical signal. Said signal maybe periodic, and may comprise a pseudo random binary sequence (PRBS) code, a Golay code, a Walsh Function, a Huffman sequence or any other suitable coded sequence. Other suitable signals, codes, or methodologies such as white Gaussian noise or wavelet analysis, may be employed.

A high power electrical signal may be applied to prevent or reduce bio-fouling thereof (i.e. the coating of the electrodes with biomass).

The electrical signal may be applied via one or more electrodes or windings which are not in direct electrical contact with the liquid. The one or more electrodes or windings which are not in direct electrical contact with the liquid may be encased within a non-conductive material, and disposed in the liquid. Alternatively, they may be positioned around the liquid. An advantage with the indirect electrical contact with the liquid is a reduction in, or elimination of, bio-fouling processes.

The impedance quantity measured may be a quantity directly related to the resonant frequency such as the dissipation factor. Data obtained in this manner are highly dependent upon the nature of the impurity, and furthermore, provide very sensitive impurity detection. An inductor may be used to adjust the resonant frequency.

A microwave electromagnetic signal may be applied to the liquid.

The method may further comprise the step of analysing the measurement of an impedance quantity with artificial intelligence means, which means may comprise an artificial neural network.

Alternatively, the method may further comprise the step of analysing the measurement of an impedance quantity with reference to a look up table.

Said steps of analysing the measurement of an impedance quantity may account for the effect of temperature on the measurement. Alternatively, the temperature of the liquid may be controlled.

The presence of one or more impurities in the liquid may be detected.

The liquid may be water, and may be a flowing source, such as a river, industrial effluent, sewage flow, tap water or a groundwater source. The method may be performed in order to detect the presence of pollutants in a water sample. On-line measurements may be made.

The analysis of the measurement of an impedance quantity may be such that normally occurring variations in the measured impedance quantity are recognised.

Measurements may be made at a plurality of locations, and data relating to the measurements may be relayed to a central location.

The liquid may be non-conductive, such as an oil. The quality of the oil may be monitored.

The presence of a microorganism in the liquid may be detected.

The liquid may be a beverage or a foodstuff.

According to a second aspect of the invention there is provided apparatus for assessing the composition of a liquid comprising:
 electrical signal applying means adapted to apply a time varying electrical signal to the liquid; and
 measuring means for measuring an impedance quantity at, or near to, the resonant frequency of an electrical circuit comprising the liquid so that the resonant frequency, or variations in the resonant frequency, can be detected.

The electrical signal applying means may apply an ac signal of variable frequency. The measuring means may comprise an impedance analyser.

Alternatively, the measuring means may perform a time to frequency domain transformation of the time varying electrical signal, which may be periodic.

The electrical signal applying means may be in direct electrical contact with the liquid.

The electrical signal applying means may comprise at least two electrodes in direct electrical contact with the liquid.

Alternatively, the electrical signal applying means may not be in direct electrical contact with the liquid. A portion of the electrical signal applying means may be encased within a non-conductive material, said portion being disposed in the liquid, or the electrical applying means may be positioned around the liquid. The electrical signal applying means (when not in direct electrical contact with the liquid) may comprise one or more electrodes, or at least two windings.

The apparatus may further comprise temperature control means adapted to maintain the liquid at a substantially constant temperature.

The apparatus may further comprise artificial intelligence means for analysing the measurement of an impedance quantity. The artificial intelligence means may be an artificial neural network.

Methods and apparatus in accordance with the invention will now be described with reference to the accompanying drawings, in which.

The invention comprises a method for assessing the composition of a liquid 10 comprising the steps of:

applying an electrical or electromagnetic signal to the liquid; and measuring an impedance quantity at, or near to, the resonant frequency of the liquid or an electrical circuit comprising the liquid so that the resonant frequency, or variations in the resonant frequency, can be detected.

Figure 1:
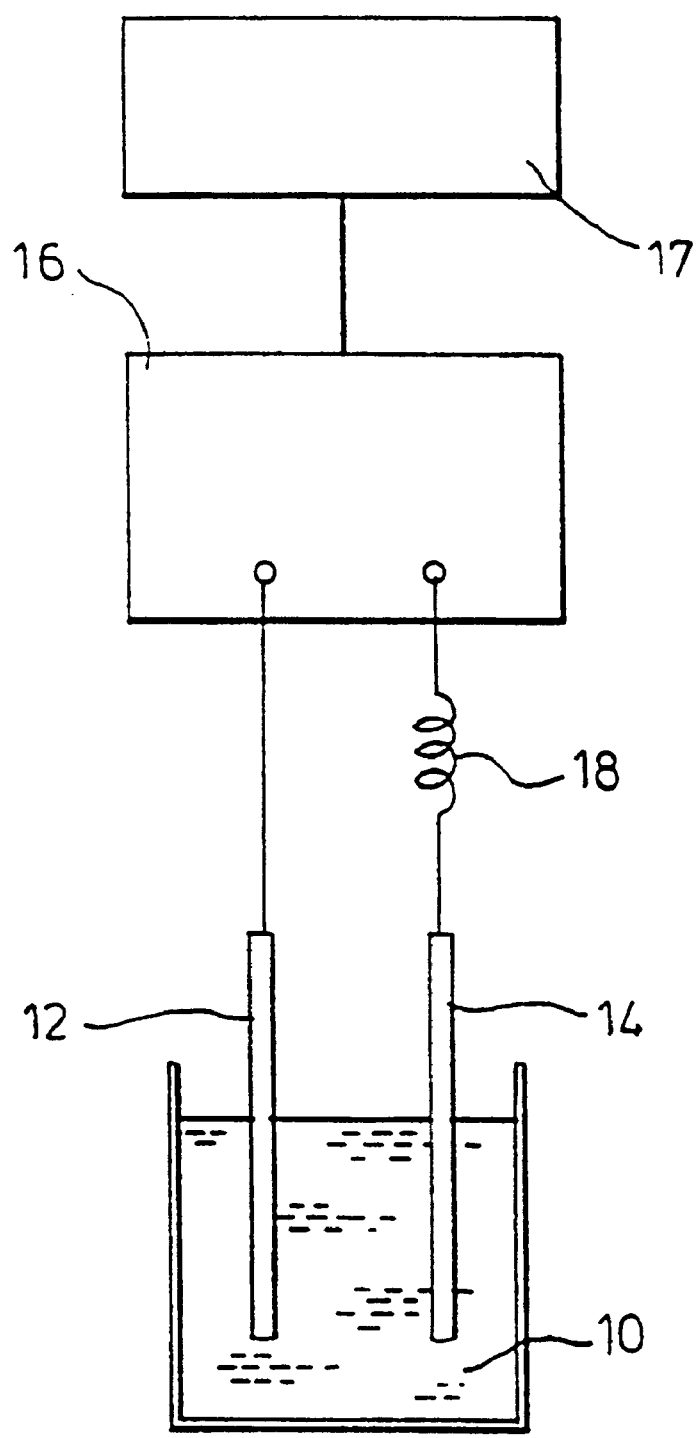
FIG. 1 is a schematic diagram of a first embodiment.

In a first embodiment, shown schematically in FIG. 1, the impedance quantity is measured as a function of the frequency of an applied electrical signal. A time varying electrical signal is applied to the liquid 10.

The time varying electrical signal is an ac signal and the frequency of the ac signal is varied. The electrical signal is applied and impedance quantities measured by an impedance analyzer 16 (Hewlett Packard 4192A) via electrodes 12, 14 disposed in the liquid 10 (and thereby in direct electrical contact with the liquid 10). Data are transferred to a personal computer 17 for analysis.

It will be apparent to one skilled in the art that, alternatively, the measurement of an impedance quantity may comprise a time to frequency domain transformation of the time varying electrical signal (see, for example, Perturbation Signals for System Identification, Ed. K Godfrey, Prentice Hill, 1993, UK). Such time-to-frequency transformation techniques are an alternative means of performing multi-frequency impedance measurements. A periodic electrical signal may be employed, which may comprise any suitable function or code, including PRBS code, Golay code, a Walsh function, or a Huffman sequence. The signal generation and processing may alternatively be based upon wavelet analysis (see, for example, Signal Processing Methods for Audio Images and Telecommunications, Eds. P M Clarkson and H Stork, Academic Press, London, 1995) or white Gaussian noise.

In either manifestation, multifrequency measurements of the impedance of the liquid are provided, a primary, but non-limiting, example of which is a sample of water. In contrast to the single measurement provided by the prior art dc conductance technique, the present invention provides a plurality of measurements within a selectable range of applied frequencies. The resulting impedance spectrum is highly dependent upon any impurity present in the water sample, providing a means for determining the type of species present in the water. Indeed, the impedance spectra may well be species selective, i.e. the precise identity of any impurity may be extracted from the technique. Additionally, as discussed in more detail below, the invention is highly sensitive. Furthermore, the invention can provide results in real time, and is substantially non-invasive.

The impedance, $Z^*$, arises from the response of the water sample to the alternating or time varying electric field stimulus, and can be considered as a type of transfer function expressing the ratio of the output voltage to input current. The transfer function is related to the composition of the water sample. In the frequency domain, the impedance is a complex quantity having a real and an imaginary component given by:

$$Z^* = R + jX$$

where R is the resistance, X is the reactance, and $j=\sqrt{-1}$.

It has proved particularly advantageous if the impedance quantity measured is a quantity directly related to the resonant frequency. The resonant frequency is the frequency at which the reactance is zero. The resonant frequency may be regarded as the frequency at which the inductive and capacitive contributions to the reactance cancel. The resonant frequency is extremely sensitive to the composition of the liquid sample. Impedance quantities directly related to the resonant frequency are those quantities having a functional form from which the resonant frequency can be directly deduced. Examples include the reactance X, which is by definition zero at the resonant frequency, and the phase angle, $\theta$, which is also zero at resonance. A particularly useful impedance quantity is the dissipation factor, DF, defined as DF=R/X. DF is a measure of the energy dissipated in the circuit, by resistive heating, to the energy stored in the circuit by capacitive and inductive mechanisms. DF is affected by the resonant frequency, since necessarily the DF reaches a maximum as X→0 (or, at least, a local maximum if there are more than one resonant frequencies). As a result, quite large dissipation factors are measured at around the resonant frequency.

It is possible to measure resonant frequencies and resonant frequency shifts without compiling a multifrequency spectrum. Phase shift oscillators, such as a three or four stage phase shift circuit, or a Wien bridge, might be used. Alternatively, a heterodyne beat method might be employed. Other methodologies would suggest themselves to one skilled in the art.

FIGS. 2 to 7 shows results obtained using the apparatus depicted in FIG. 1 to measure the impedance of numerous water samples. The electrodes 12, 14 are platinum wires. It has proved advantageous to include an inductor 18 in series with the electrodes 12, 14. The inductor 18 ensures that the circuit comprising the arrangement of FIG. 1 resonates. Furthermore, the value of the inductor 18 used (324 $\mu$H), is such that the resonant frequency occurs within a tractable frequency range, i.e around 1 MHz or less. At such frequencies, problems associated with instrumentation and digitisation are reduced. Quartz crystal resonators, or other such means, might alternatively be employed to affect the resonant frequency of the circuit. The applied voltage is 0.2 V peak to peak, the amplitude of the voltage being kept relatively small in order to prevent electrochemical reactions occurring.

Figure 2:
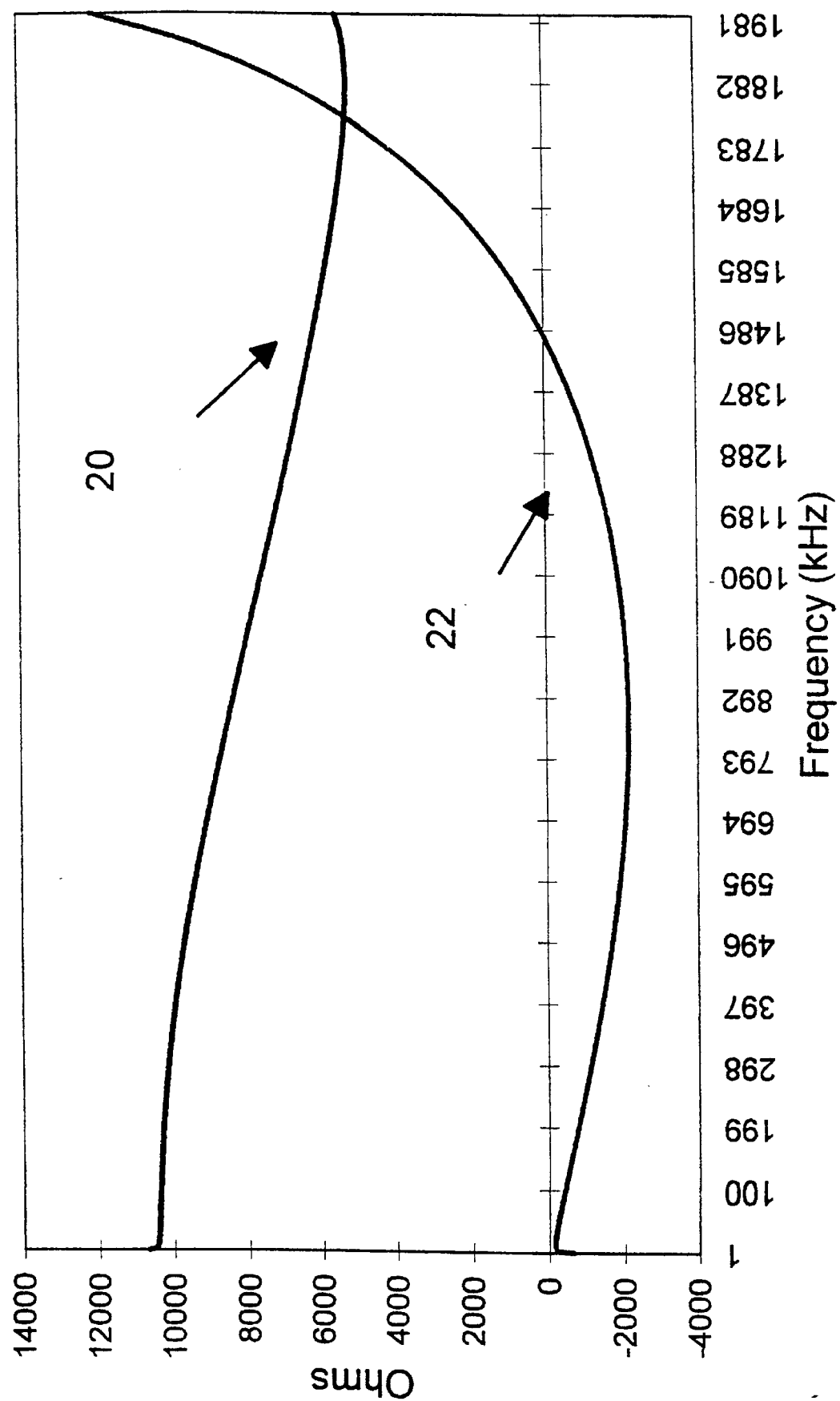
FIG. 2 shows resistive and reactive components of a sample of tap water as a function of frequency.

FIG. 2 shows the resistive 20 and reactive 22 values of a sample of domestic tap water recorded as a function of frequency in the range 1 to 1981 kHz. The reactive part 22 crosses the abscissa at ca. 1500 kHz.

Figure 3:
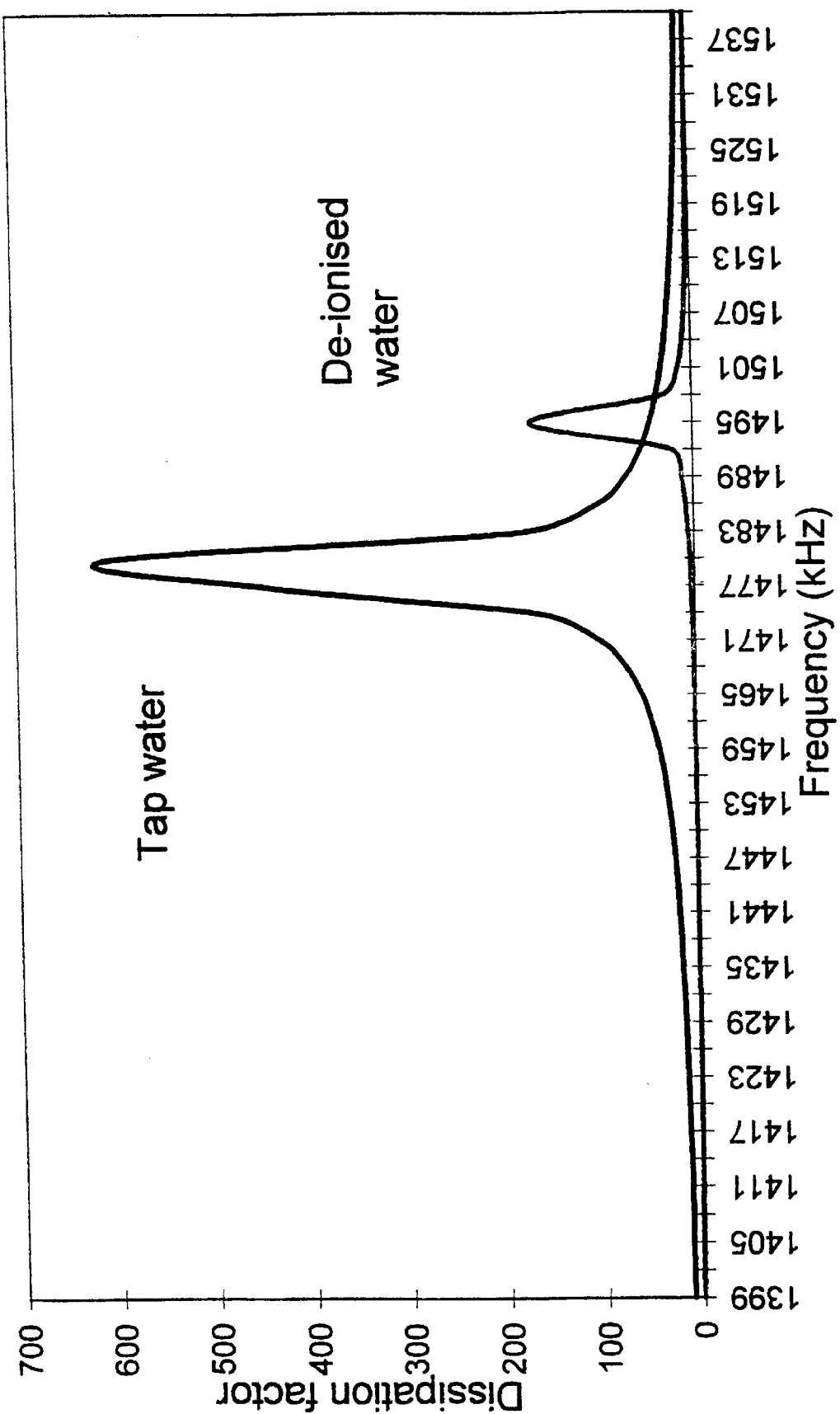
FIG. 3 shows dissipation factor as a function of frequency for samples of tap water and de-ionised water.

FIG. 3 shows the dissipation factor for the samples of tap water and also for a sample of HPLC grade de-ionised water. Clearly, there are significant differences in both the value of the resonant frequency—equivalent to the frequency at which the dissipation factor reaches a maximum value—and the magnitude of the maximum value itself. An upward shift in resonant frequency of ca. 15 kHz is discernible in FIG. 2 when de-ionised water is used on place of tap water. It is noted that the upward frequency shift is accompanied by an apparent reduction in the maximum value of the dissipation factor. A cautionary note should be struck here. The maximum calculated value of the dissipation factor is critically dependent upon a value of the reactance that is approaching zero. Thus, the calculated value of the dissipation factor maximum is dependent upon the frequency step size employed and its proximity to the true resonant frequency. The latter quantity is likely to be temperature dependent. Notwithstanding these comments, it is believed that the magnitude of the dissipation factor will provide useful information additional to that provided by the resonant frequency.

Figure 4:
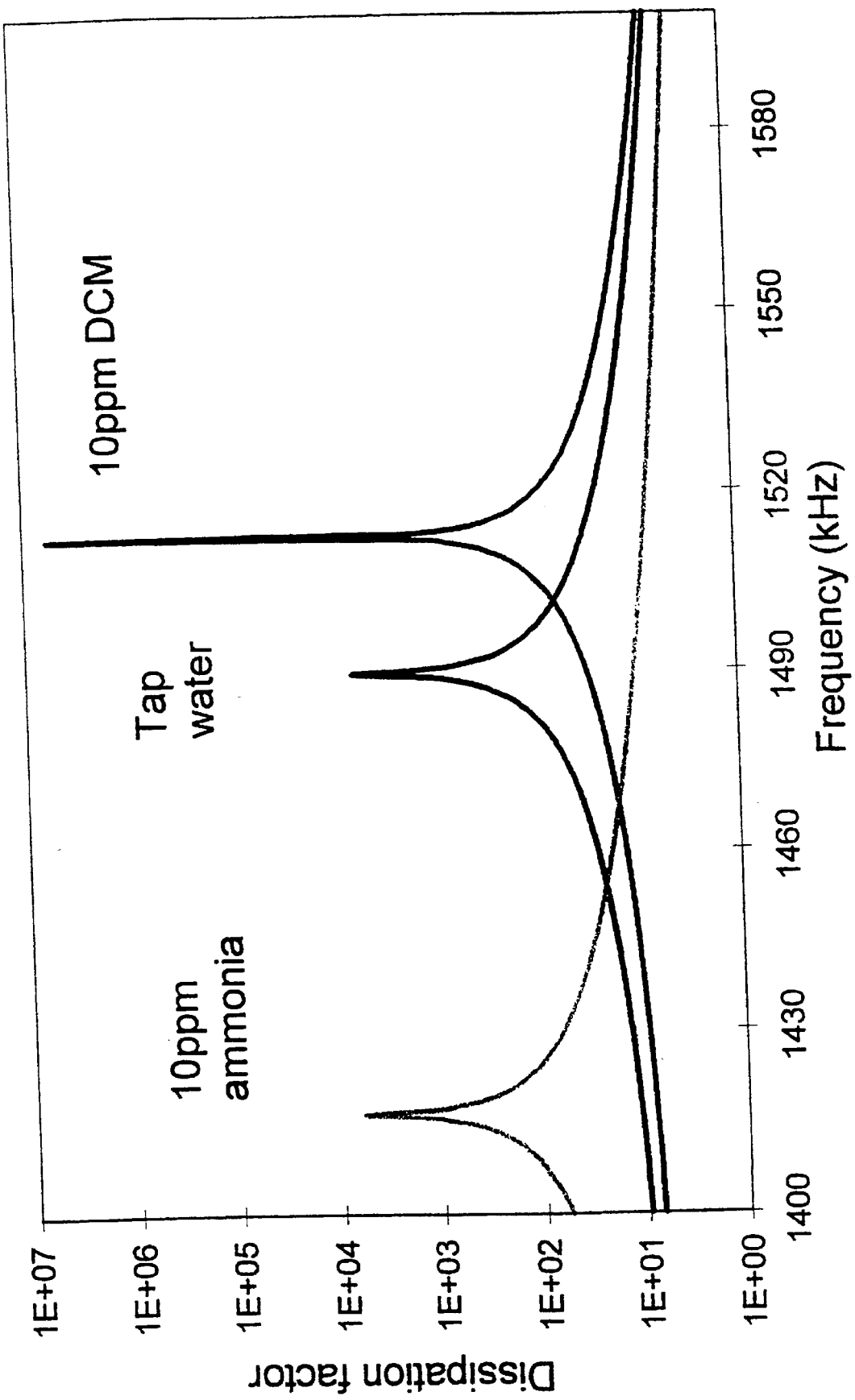
FIG. 4 shows dissipation factor as a function of frequency for a sample of tap water with pollutants added thereto.
Figure 5:
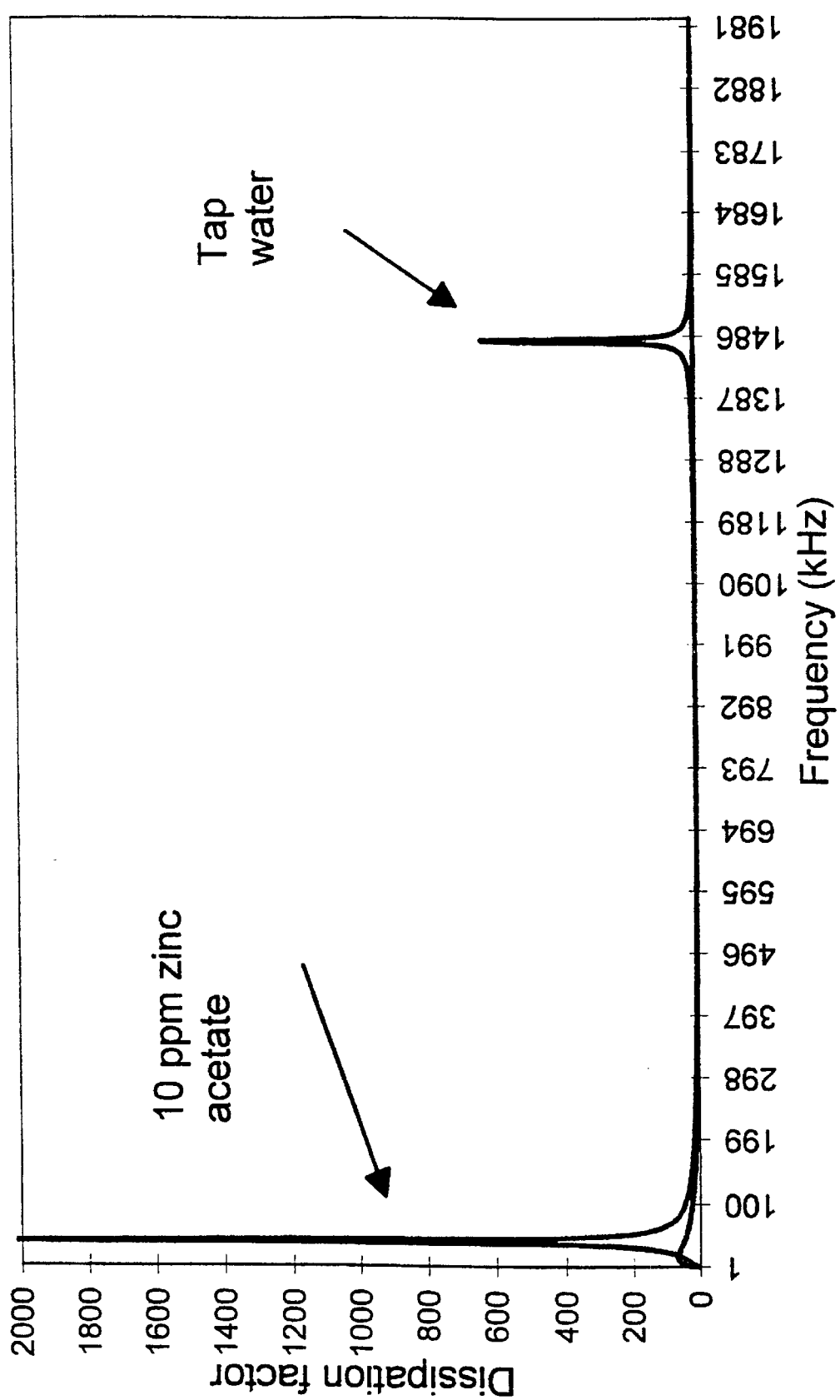
FIG. 5 shows the effect of zinc acetate on the dissipation factor of tap water.

FIGS. 4 and 5 show the effects of adding various pollutants to the sample of tap water. The addition of 10 ppm dichloromethane (DCM) results in an upward shift of the resonant frequency of 24 kHz (FIG. 4). The addition of 10 ppm ammonia results in a downward resonant frequency shift of 72 kHz (FIG. 4). FIG. 5 shows the effect of 10 ppm of zinc acetate: a dramatic downward shift of ca. 1450 kHz.

Figure 6:
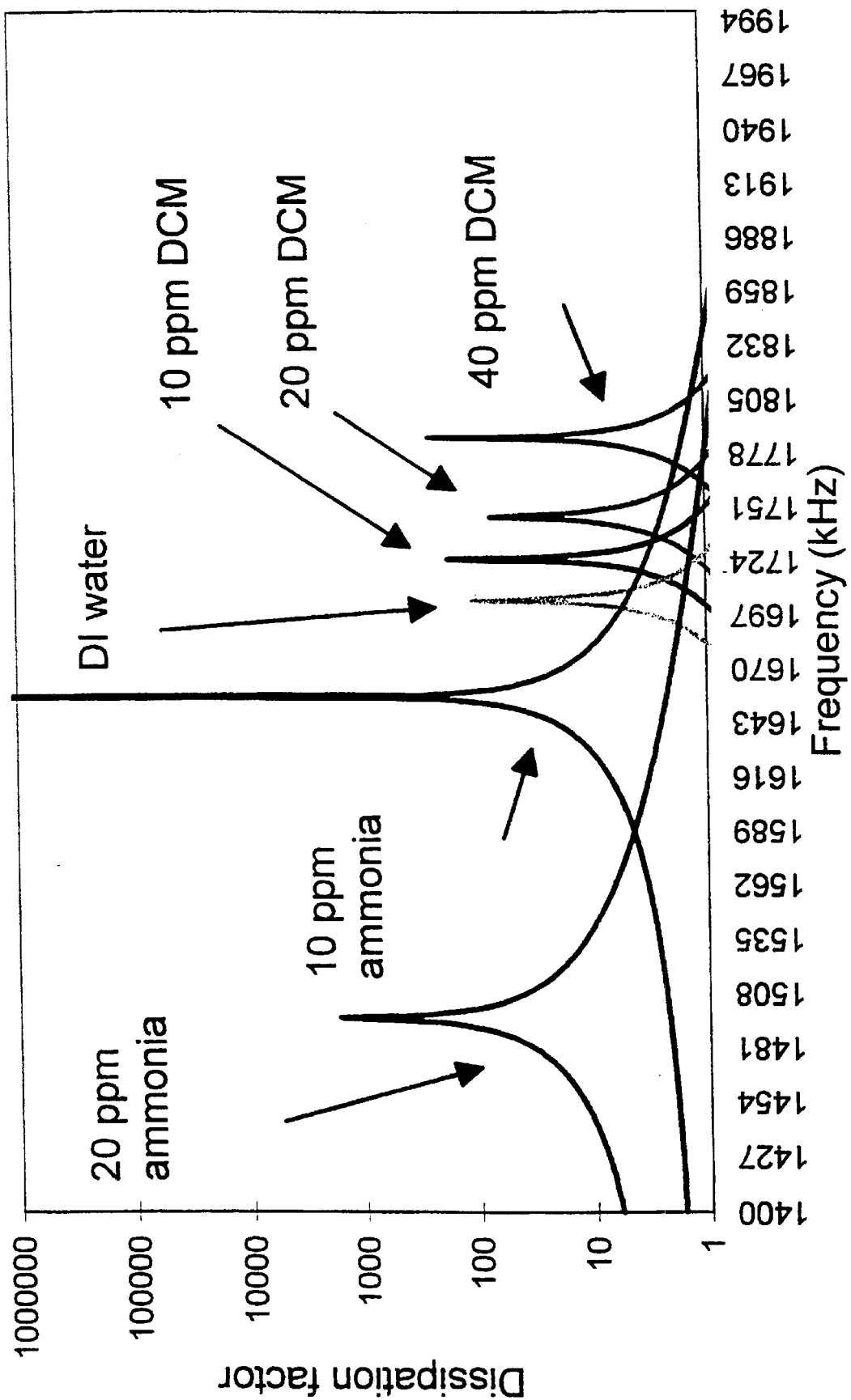
FIG. 6 shows the effects of varying the concentration of pollutants on the dissipation factor of de-ionised water.

FIG. 6 shows the effects of adding DCM and ammonia of differing concentrations to de-ionised water. Clearly the magnitude of the shifts in resonant frequency increase as concentration increases. Addition of 10, 20 and 40 ppm of DCM to the de-ionised water sample appears to result in upward resonant frequency shifts which are proportional to the DCM concentration.

Figure 7:
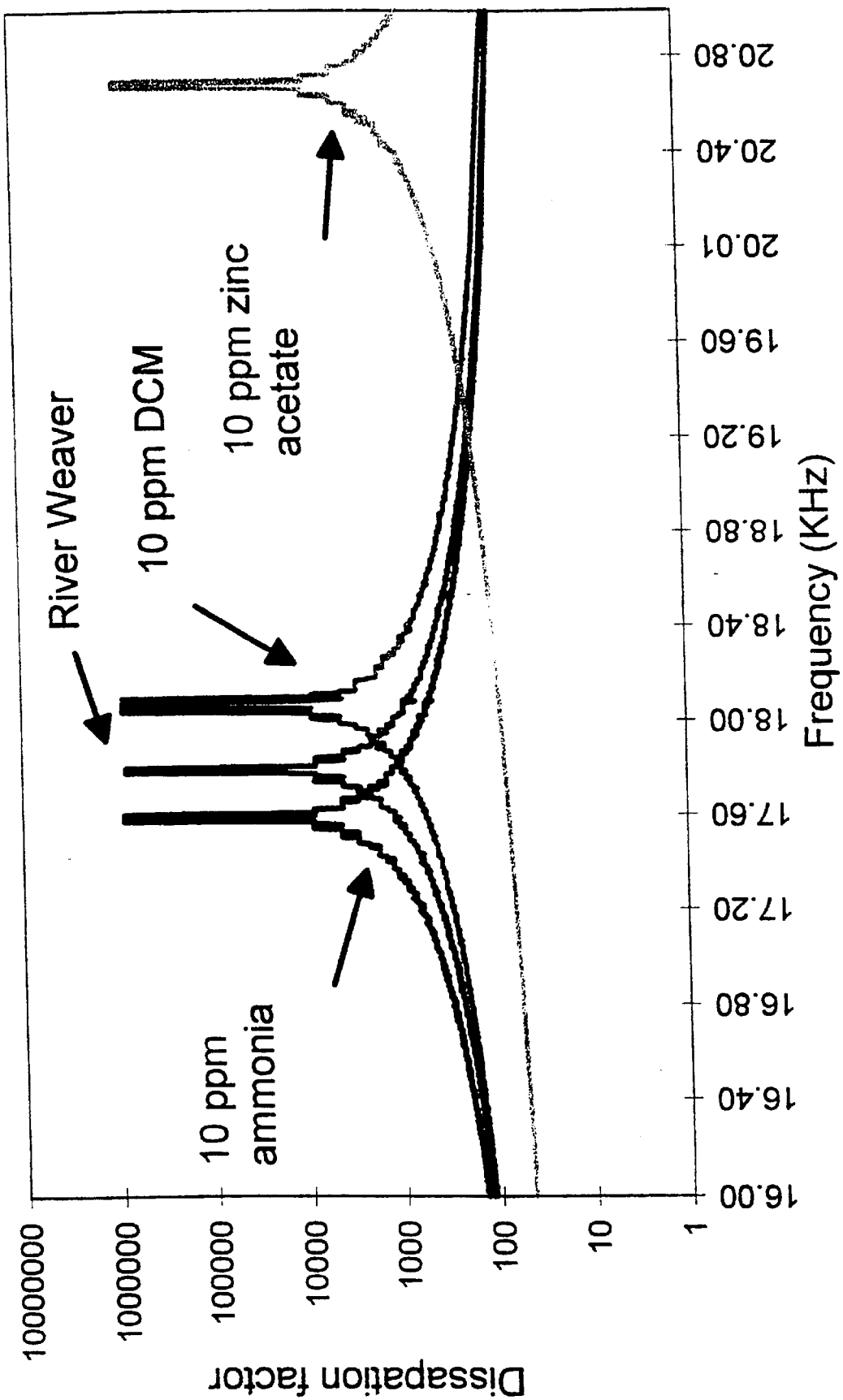
FIG. 7 shows the effects of pollutants on the dissipation factor of a sample of river water.

FIG. 7 shows the results of measurements performed upon samples of water taken from the River Weaver, Cheshire, UK. Water from the River Weaver exhibits a resonant frequency at ca. 17.8 kHz. This is considerably lower than the resonant frequencies obtained with de-ionised water and tap water. Although the composition of the River Weaver water is not known, it is tempting to speculate that the dramatic reduction in resonant frequency is due to the presence of certain pollutants, of an as yet uncharacterised nature, in the river water. Such a conclusion would not be inconsistent with the presence of a great deal of heavy industry in the vicinity of, and upstream of, the site where the water sample was collected. FIG. 7 also shows the effect of adding pollutants to the river water sample. The addition of 10 ppm of ammonia causes a shift in the resonant frequency to lower frequency, whilst the addition of 10 ppm of DCM causes an opposite shift in resonant frequency, to higher frequency. The directions of these resonant frequency shifts are the same as those observed with tap water and de-ionised water. Addition of 10 ppm zinc acetate produces an upward shift in resonant frequency, the magnitude of which is large compared to the shifts observed with ammonia and DCM. Although the physical mechanisms behind the observed frequency shifts are not, at present, well understood, it is quite sufficient for the present purposes that information about the nature and concentration of any impurities present in the water sample can be empirically derived from multifrequency impedance measurements.

Figure 8:
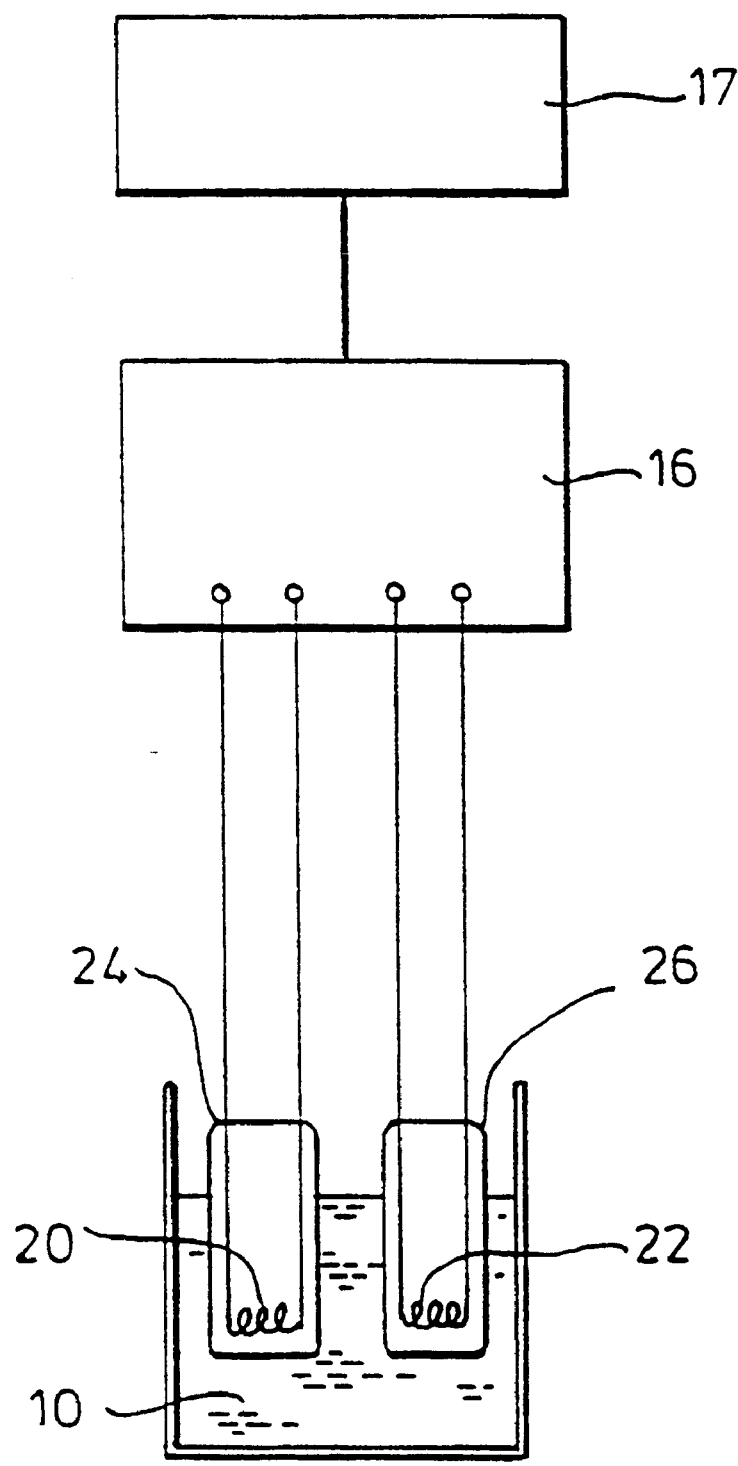
FIG. 8 is a schematic diagram of a second embodiment.

FIG. 8 shows a second embodiment of the invention. The apparatus shares some common elements with the first embodiment, which is indicated by the use of common reference numerals in FIGS. 1 and 2. In the second embodiment, a pair of windings 20, 22 are employed in place of the electrodes 12, 14 of the first embodiment. The windings 20, 22 are potted in casings of an inert material 24, 26, such as PTFE, and act in a similar manner to a transformer. Thus, one winding 24 is energised as a primary winding, and drives the other winding 26, which acts as a secondary winding. A current is included in the secondary winding with an efficiency which depends on the impedance of the medium between the two windings.

An advantage of this embodiment is a reduction in the extent and the effect of bio-fouling and corroding processes. Since the windings 20, 22 are not in direct contact with the water 10, direct bio-fouling of the windings 20, 22 does not occur. Bio-fouling of the casing 24, 26 will occur, but the operation of technique is not affected so readily as is the case with the first embodiment. Such bio-fouling may be eliminated if a thin coating of a bio-toxic metal such as copper or silver is present on the casing. Alternatively, it is in principle possible to position the casings 24, 26 out of direct contact with the liquid to be analysed. In this way bio-fouling of the casings 24, 26 would be eliminated. However, in practice, the separation of the windings should be of the order of 1 cm making such positioning difficult unless the liquid flows between the windings in a narrow channel, such as a flow tube. It may be possible to make measurements of liquids in pipes, although a problem is encountered if, as is often the case, the pipe is conductive, i.e. metallic. This problem is overcome if a non-conducting insert, such as a plastic insert, is suitably positioned in a portion of the pipe.

Figure 9:
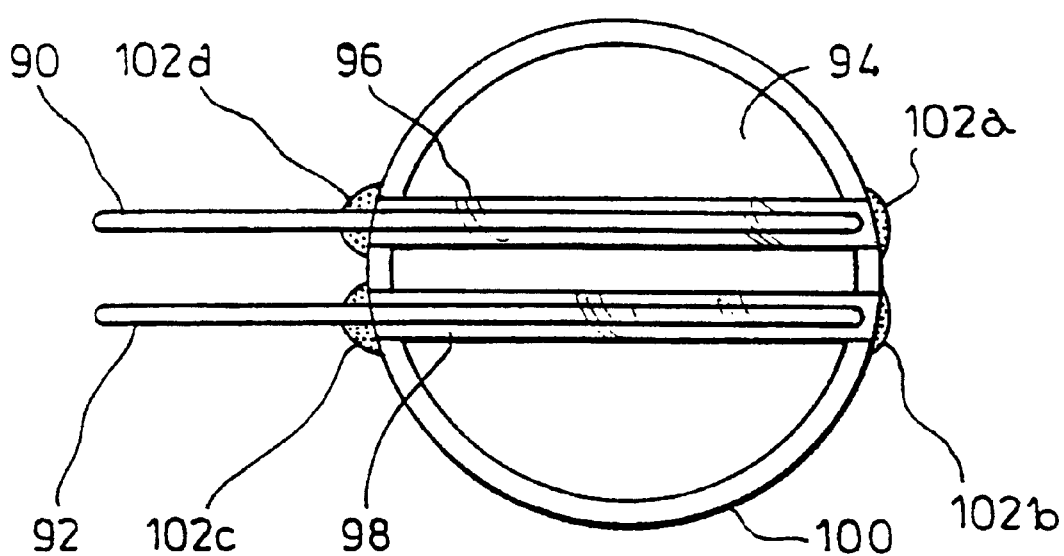
FIG. 9 shows the electrode arrangement of a third embodiment.
Figure 10:
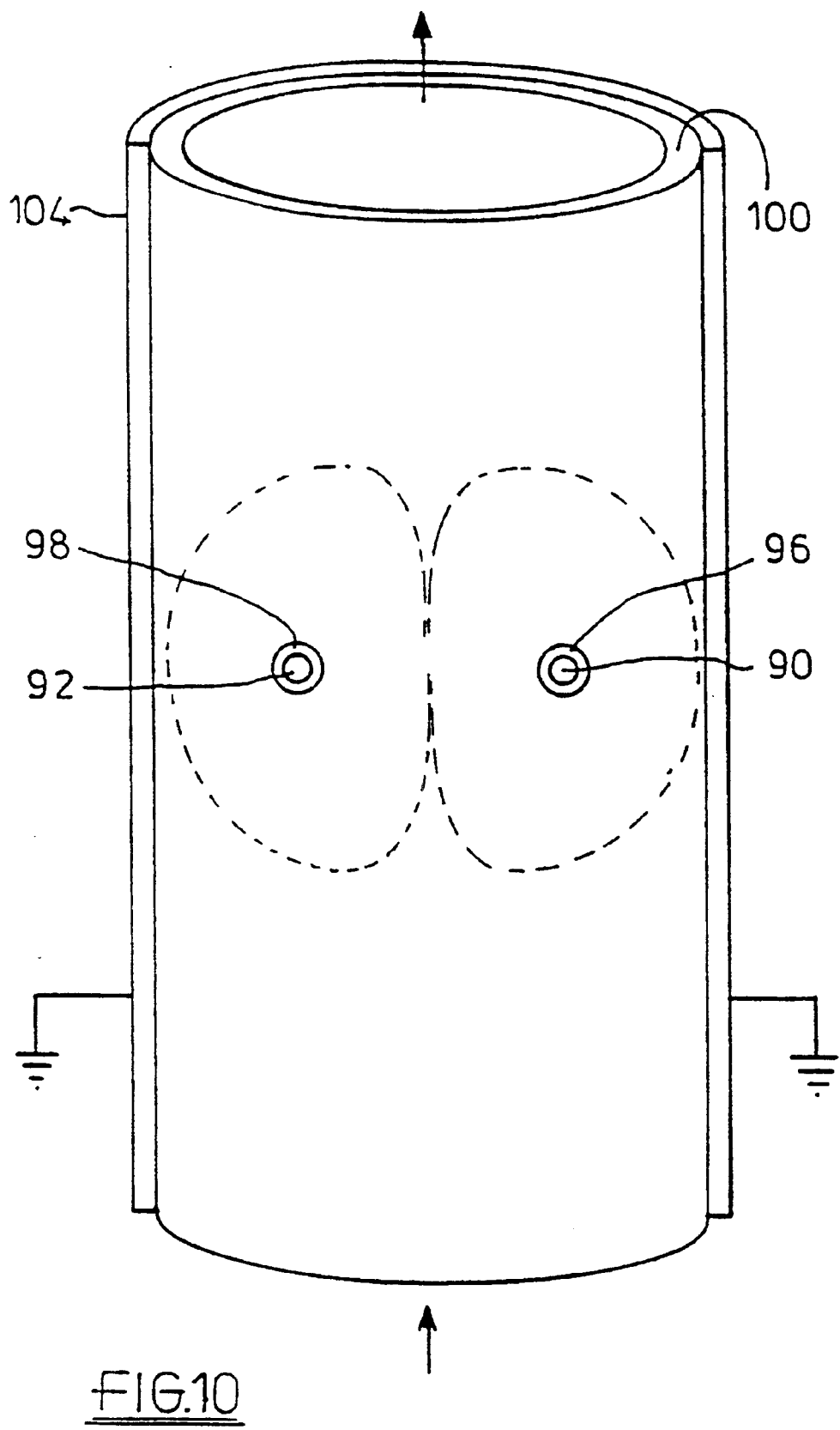
FIG. 10 shows the likely electric field distribution around the electrodes of FIG. 9.
Figure 11:
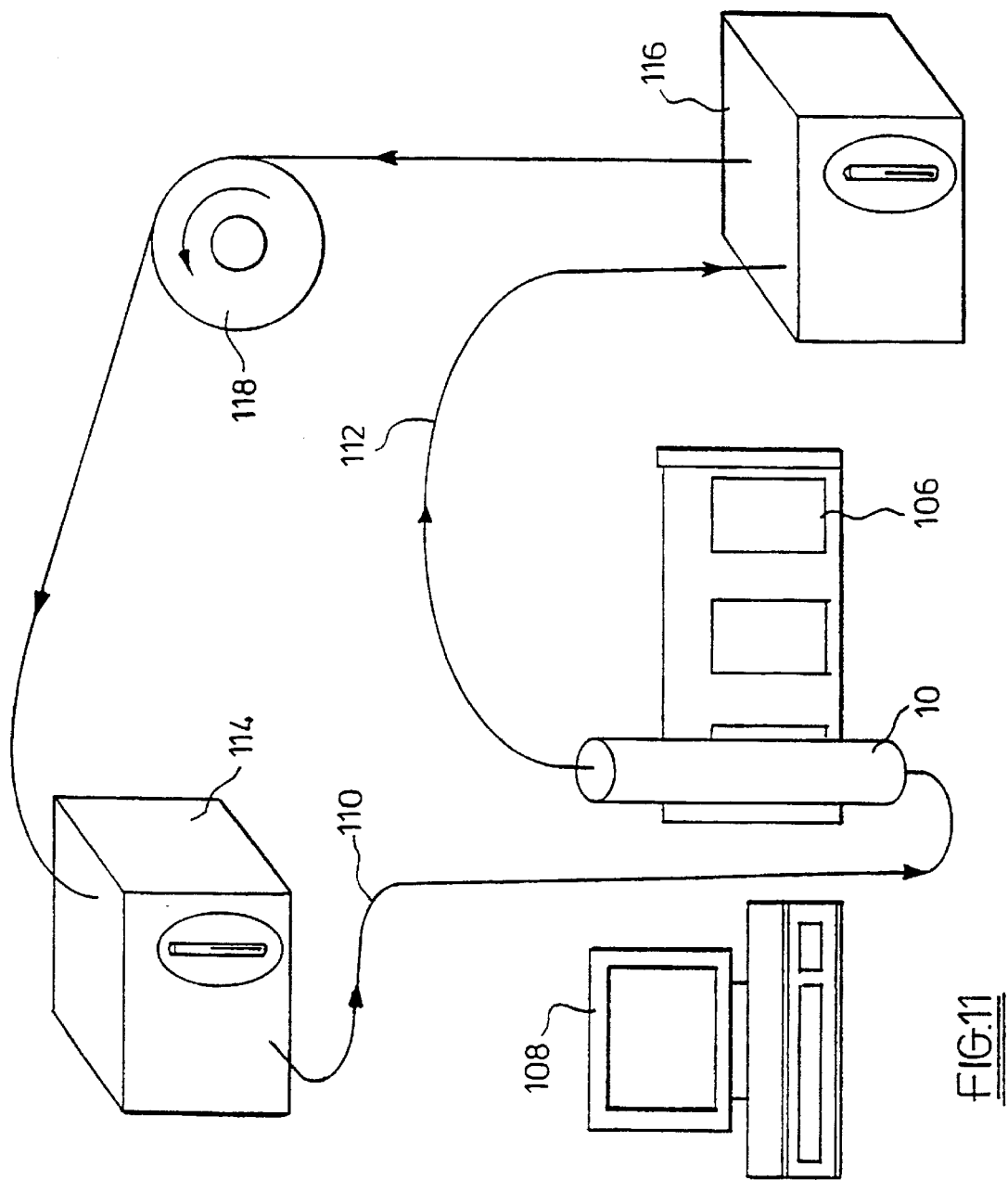
FIG. 11 is a schematic diagram of the third embodiment.

FIGS. 9 to 11 show a third embodiment of the invention in which electrodes 90, 92 are employed which are not in direct electrical contact with the liquid 94. An advantage with this configuration is that the extent of corrosion or bio-fouling is reduced or eliminated. A further advantage is that relatively high potential differences can be applied to the electrodes without the risk of inducing electrochemical reactions.

The two electrodes 90, 92 are formed from copper, although many other suitable conductive materials will suggest themselves to those skilled in the art. The electrodes 90, 92 are each introduced into a tube of glass 96, 98. The glass tubes 96, 98 are then inserted into a tubular member 100 (fabricated in plexy glass) via suitable apertures 102 a,b,c,d, formed by drilling the tubular member 100. The apertures were rendered water tight using a suitable sealant. A 0.05 mm thick stainless steel sheet 104 is rolled around the tubular member 100, the sheet 104 being grounded to i) shield the apparatus from any interference which might perturb the electric field generated by the electrodes 90, 92 and ii) retain this electric field within the vicinity of the tubular member 100. FIG. 10 shows the likely electric field distribution, with regions of higher electric field being depicted in darker shades.

Electrical signal is applied to the electrodes 90, 92 and impedance quantities measured by an impedance analyzer 106 (Hewlett Packard 4192A) in series with a inductor (not shown) the value of which is selected so as to produce a circuit resonant frequency of ca. 1 MHz. Data are transferred to a personal computer 108 for analysis.

Two water pipes 110, 112 are connected to the tubular member 100, with the water inlet at the bottom and the water outlet at the top to reduce the formation of water bubbles. The water circulation circuit further comprises a water supply tank 114, placed at a higher level than the tubular member 100 to maintain a constant water pressure, a drain tank 116 and a pump 118 to pump water from the drain tank 116 to the supply tank 114.

The drain tank 116 is filled with distilled water and the pump 118 is run at 1.15 l min$^{-1}$, the water being circulated for 10 minutes. Measurements of the resistive and reactive parts of the impedance are measured using a frequency sweep from 1700 kHz to 1900 kHz in frequency increments of 0.2 kHz, a range which encompasses the resonant frequency of the circuit Three measurements were made on the distilled water sample, and then three measurements each were made on a 10 ppm solution of commercially available tomato food in distilled water and 100 ppm tap water in distilled water. The composition of the tomato food is as follows:

N—P—K fertiliser 6-5-9, Total Nitrogen (N) 6%, Phosphorous pentoxide solution in neutral ammonium nitrate and water 5% (2.2%P), potassium oxide ($K_2O$) soluble in water 9% (7.5%K) and trace amounts of magnesium oxide (MgO) 333 mg kg$^{-1}$.

Figure 12:
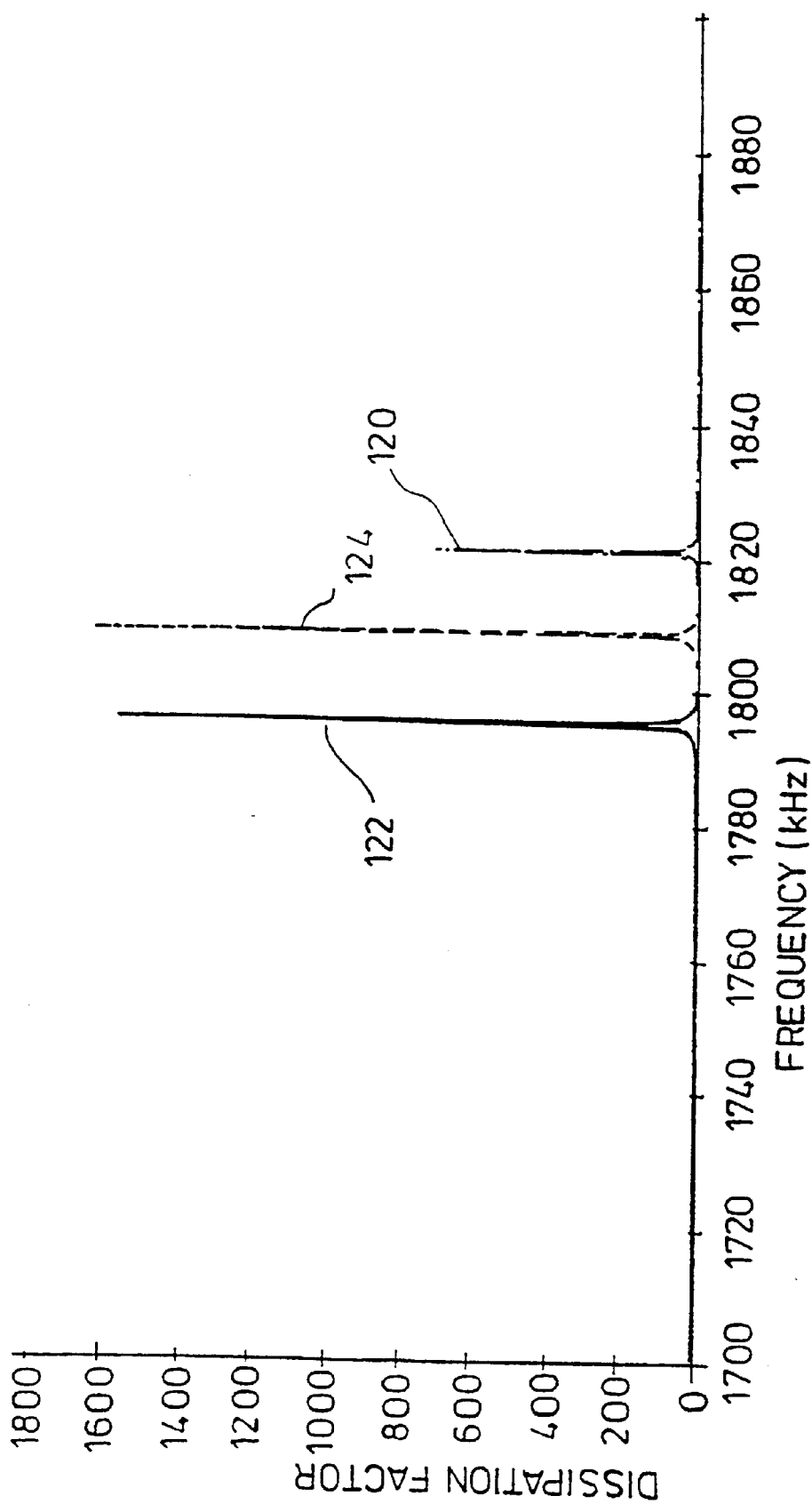
FIG. 12 shows dissipation factor for samples of distilled water, tomato food solution and tap water.

FIG. 12 shows dissipation factor against frequency, obtained from measurements of the distilled water 120, tomato food solution 122 and tap water solution 124. Excellent discrimination is obtained, with distinct resonant frequencies being observed at 1821.2, 1795.4 and 1808.6 kHz for the distilled water, tomato food solution and tap water solution measurements respectively. Measurement repeatability is excellent and sensitivity is high.

Figure 13:
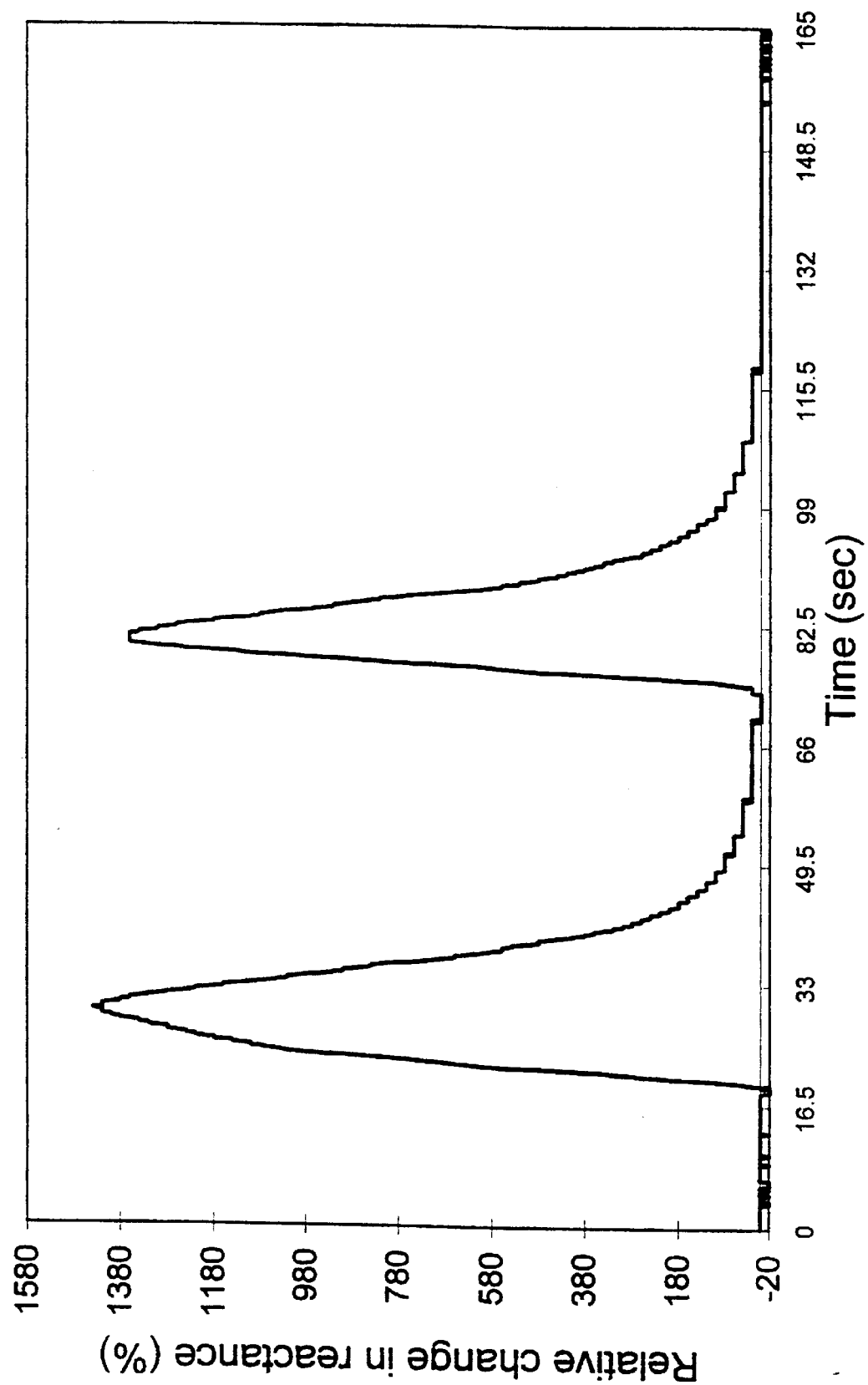
FIG. 13 shows the kinetic response of the third embodiment.

The kinetic response of the system was assessed by continually flushing tap water through the tubular member, and injecting 20 ml of contaminated water (distilled water exposed to corroded metal) into the running tap water. The frequency of the electrical signal applied by the impedance analyzer is 1808.6 kHz, this figure being the resonant frequency of the system with the tap water running therethrough. FIG. 13 measured reactance as a function of time whilst two injections of contaminated water were performed. Relative reactance changes of ca. 1400% are observed, this response being rapid (10 to 15 seconds, depending on flow rate).

Figure 14:
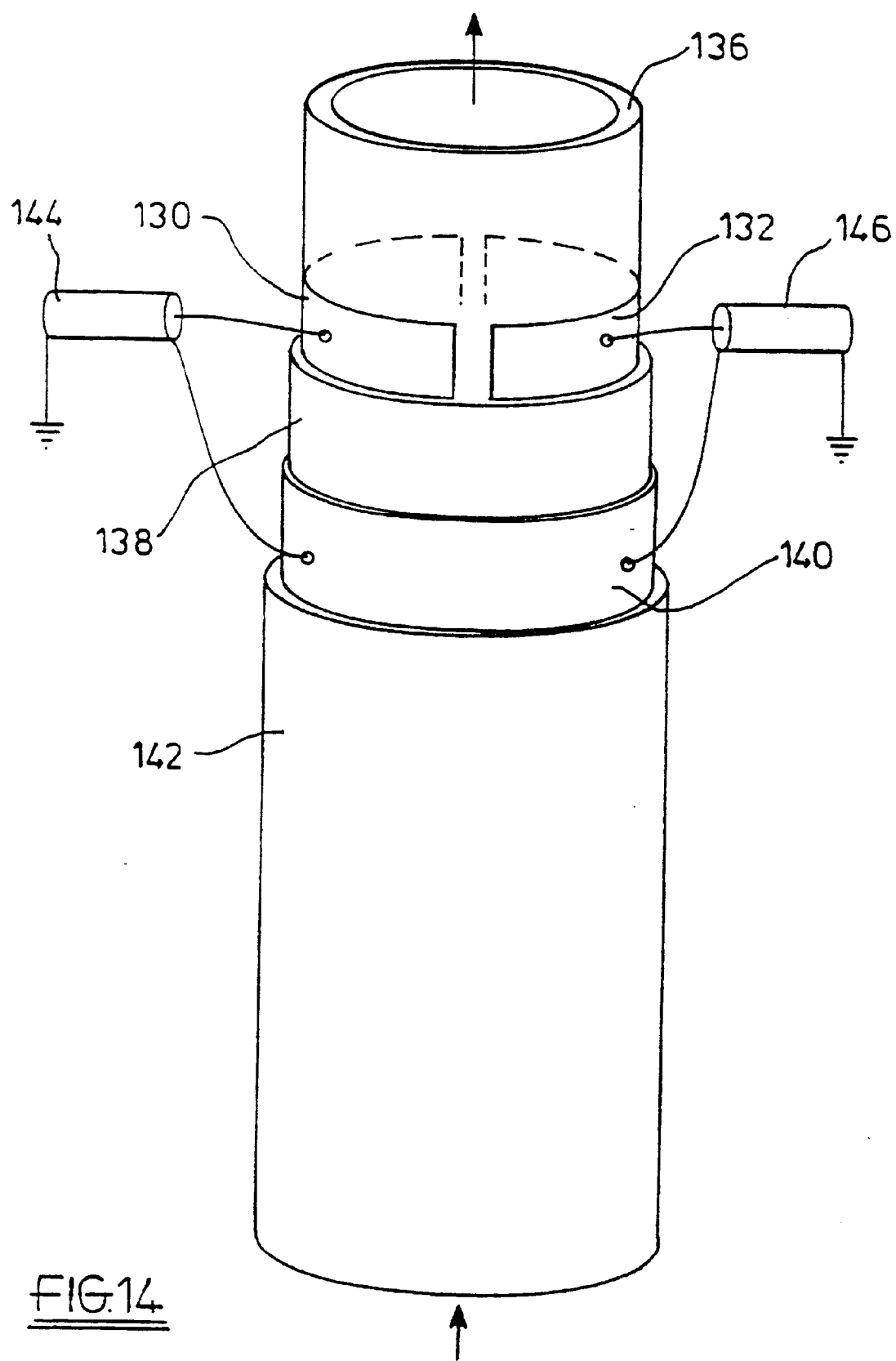
FIG. 14 shows the electrode arrangement of a fourth embodiment.

FIG. 14 shows a fourth embodiment of the invention in which electrodes 130, 132 are employed which, in addition to not being in direct electrical contact with the liquid 134, are actually positioned around the liquid, rather than being disposed therein.

The electrodes 130, 132 are stainless steel plate electrodes of 0.05 mm thickness, which are positioned on adjacent sides of a tubular member 136 (fabricated from plexy glass). The tubular member 136 acts as a conduit for the flow of water and is of ca 2.5 cm diameter. The electrodes 130, 132 are held in place and protected by a PVC sleeve 138 having an inside diameter slightly larger than the outside diameter of the tubular member 136. A stainless steel ground plate 140 is disposed around the PVC sleeve 138 so as to envelope the entire arrangement, the ground plate 140 being grounded to shield the device from stray electrical fields, and to retain the electric field generated by electrodes 130, 132 within the vicinity of the tubular member 136. A further PVC sleeve 142 is fitted over the ground plate 140.

Figure 15:
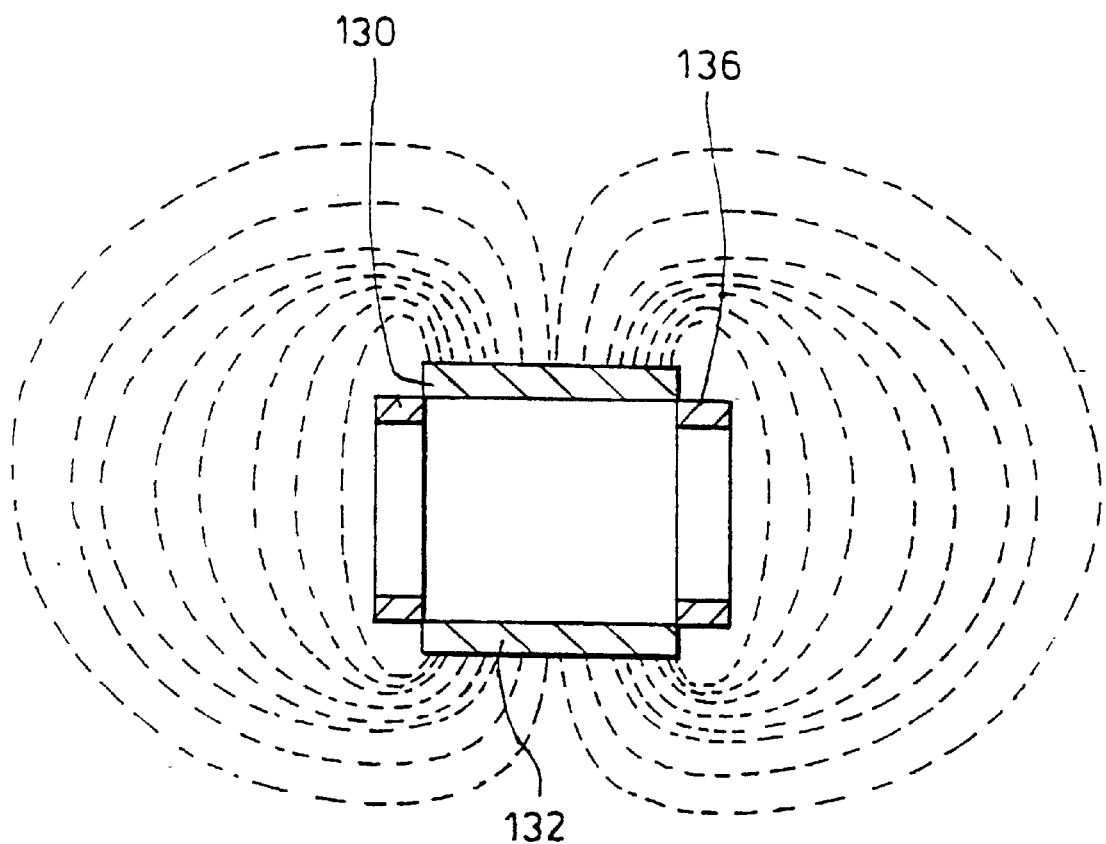
FIG. 15 shows the likely electric field distribution around the electrodes of FIG. 14.

The electrodes 130, 132 are connected to an impedance analyzer (Hewlett Packard 4192A) via coaxial cables 144, 146 which are also used to ground the ground plate 140. FIG. 15 shows the likely electric field distribution when a potential difference exists between the electrodes 130, 132, indicating that the device acts like a plate capacitor device. The impedance of the walls of the tubular member 136 and the liquid 134 are measured at a plurality of applied frequencies, thereby allowing detection of changes in the composition of the liquid.

The device shown in FIG. 14 was connected to the distilled water circulation system and detection system previously described with regard to the third embodiment of the invention and depicted in FIG. 11. An inductor was connected in series with the impedance analyzer to produce a circuit resonant frequency of ca. 1 MHz Measurements of the resistive and reactive parts of the impedance are measured using a frequency sweep of 2 kHz from 1053 kHz to 1055 kHz in frequency increments of 0.2 kHz, a range which encompasses the resonant frequency of the circuit. Three measurements were made on each of four water samples, namely distilled water and 1 ppb, 10 ppb and 20 ppb solutions of tomato food in distilled water. The composition of the tomato food is detailed above in respect of the previous embodiment.

Figure 16:
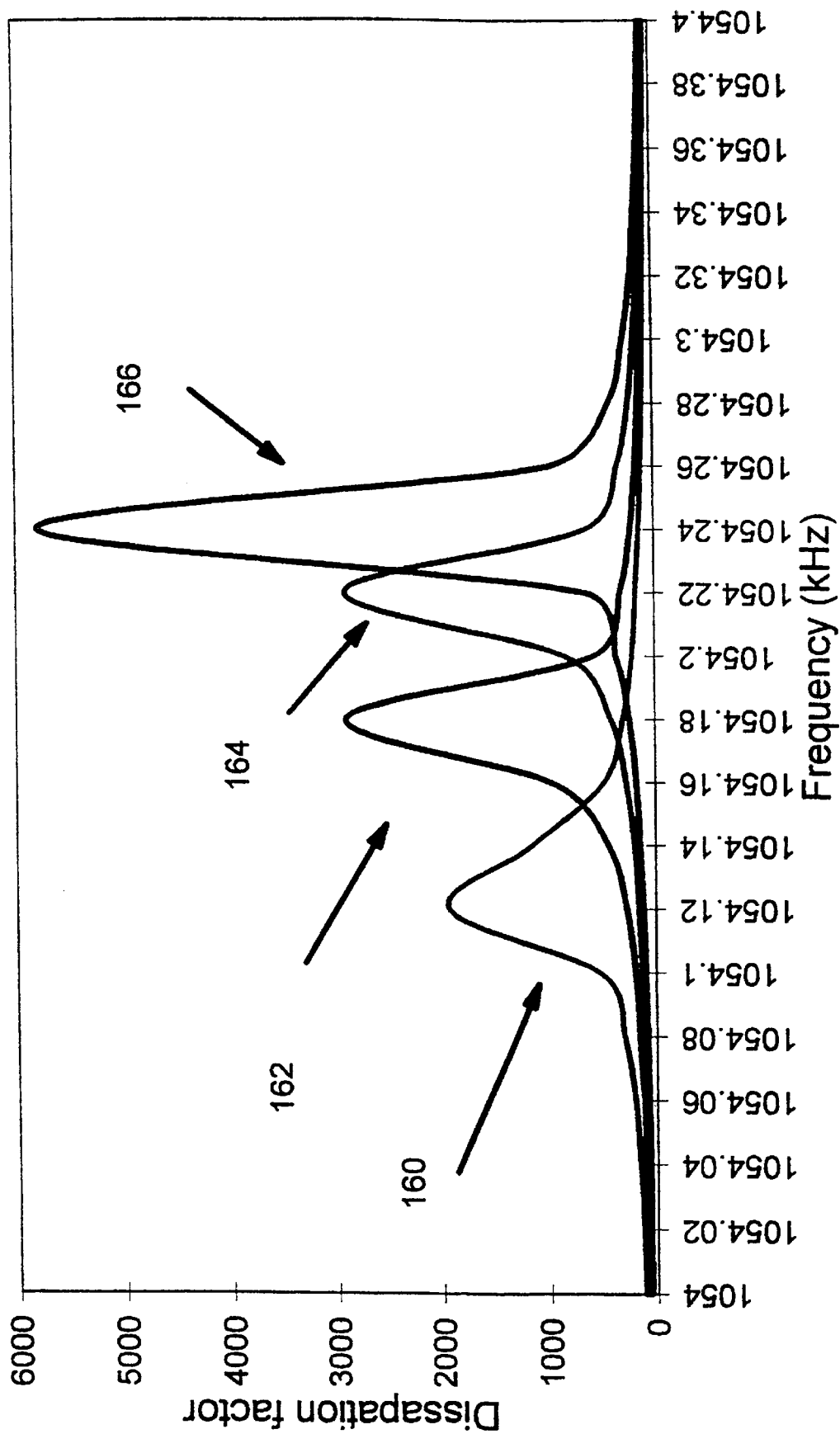
FIG. 16 shows dissipation factor for distilled water and various tomato food solutions.

FIG. 16 shows dissipation factor against frequency obtained from measurements of the distilled water 160, 1 ppb tomato food solution 162, 10 ppb tomato food solution 164 and 20 ppb tomato food solution 166. The resonant frequency of the device with distilled water is 1054.12 kHz. The presence of 1 ppb tomato food solution causes an increase in resonant frequency of about 60 Hz. Higher concentrations of tomato food produce shifts in the resonant frequency to higher frequencies still, although the frequency shifts appear to be non-linear with respect to the concentration. Measurement repeatability is good, and the ability to detect a 1 ppb solution of a contaminant indicates that sensitivity is excellent. The kinetic response of the system was measured in the manner previously described with respect to the third embodiment of the invention. Samples of distilled water and a 10 ppm tomato food solution in distilled water were injected. The impedance analyzer applied an electrical signal of 1046 kHz—the resonant frequency of the device with tap water running. Relative reactance changes of ca. 3500% and 250% are observed for the tomato food solution and distilled water injections, respectively. Response times are in the range 10 to 15 seconds, indicating that on-line measurements in real time are feasible.

The tubular member should be non-conductive. If measurements of liquid flowing in a metallic pipe were required, a suitable section containing a non-conductive tubular member could be installed into a section of the pipe. Many pipes are fabricated in rubber or polymeric material—particularly in domestic applications—and thus implementation of the invention would be even more straightforward.

Figure 19:
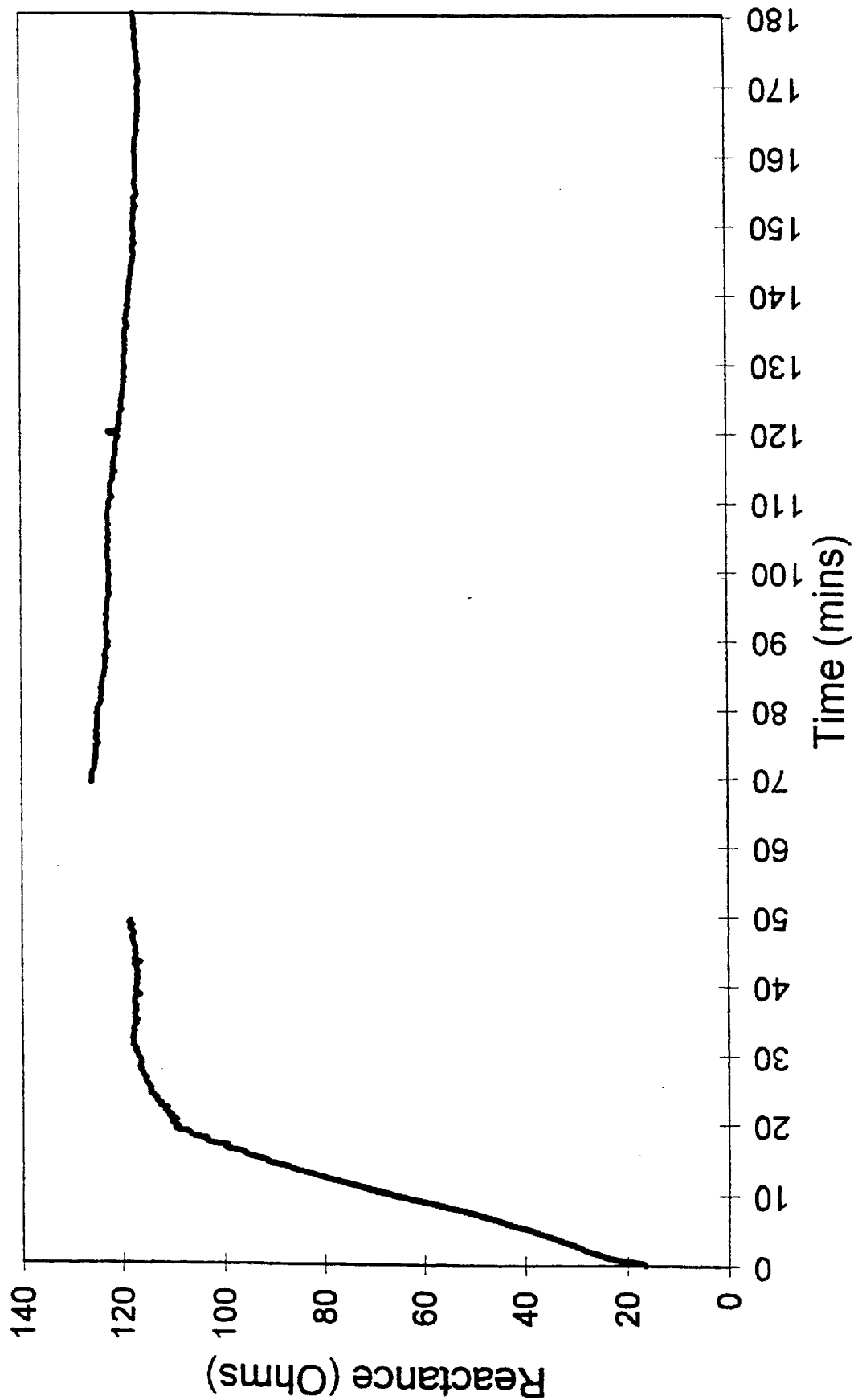
FIG. 19 shows reactance against time for a yeast solution.
Figure 20:
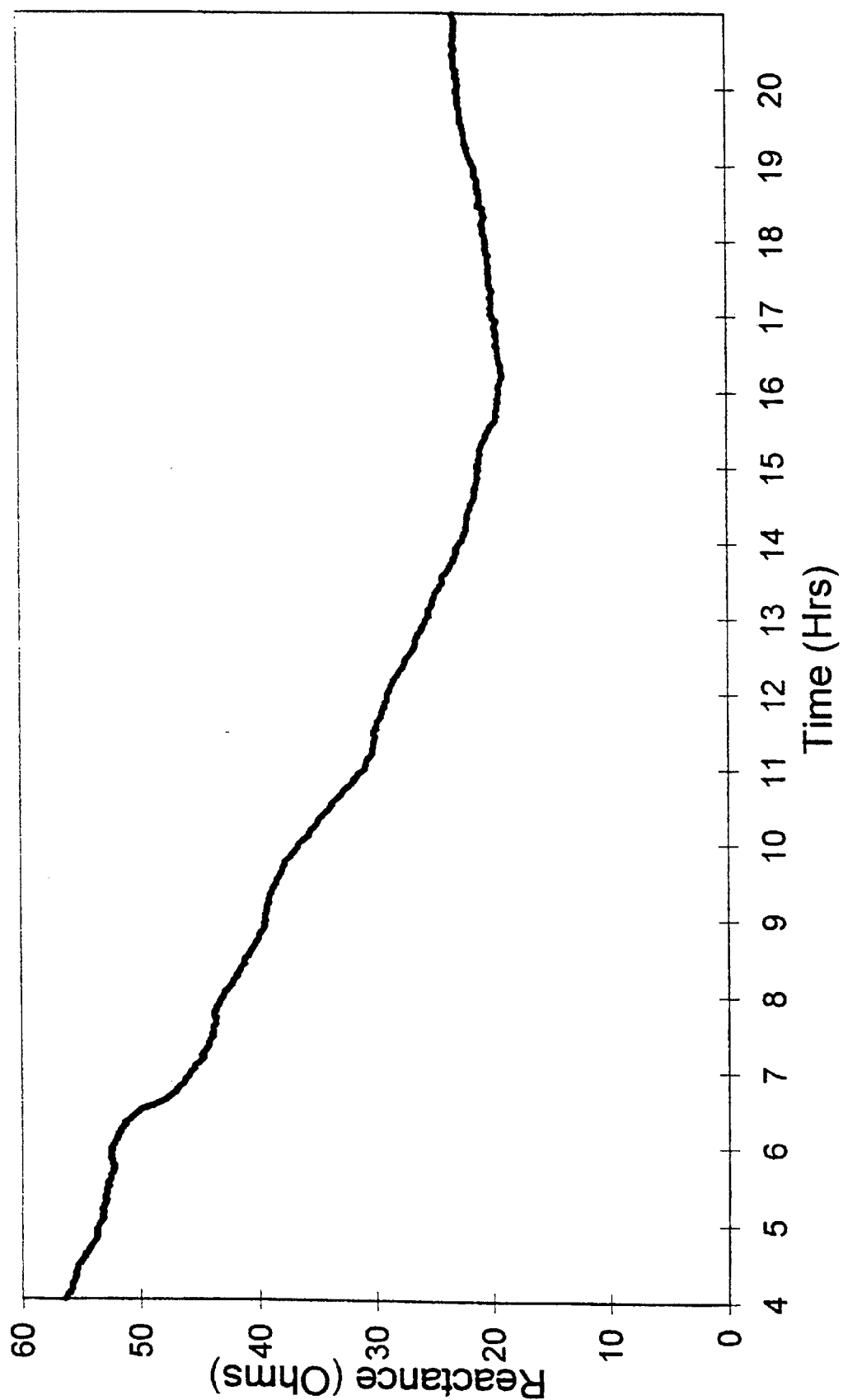
FIG. 20 shows reactance against time for a sample of milk.
Figure 21:
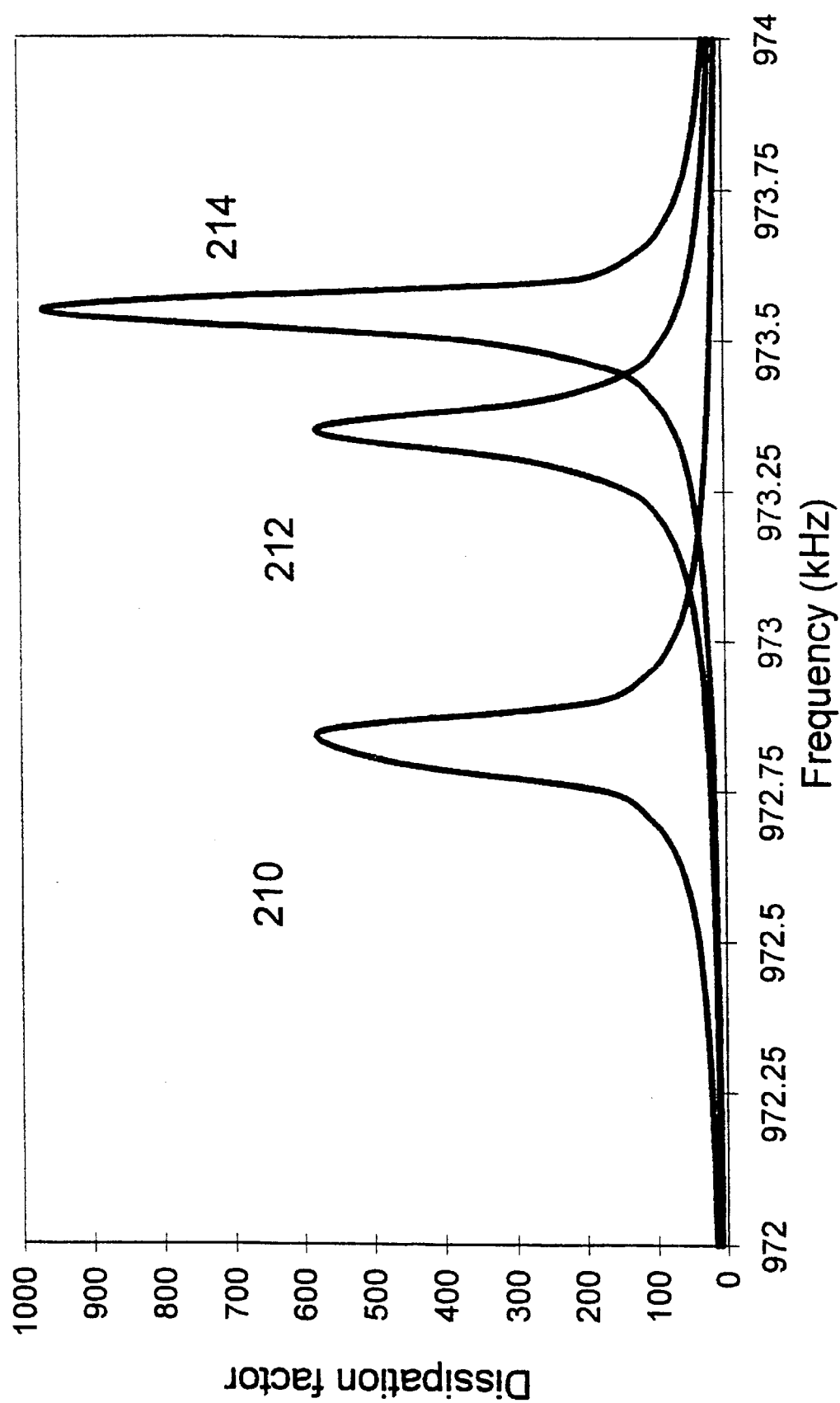
FIG. 21 shows dissipation factor for various samples of cola.

The device shown in FIG. 14 was adapted to contain a sample of liquid, rather than act as a conduit for a flowing sample. FIGS. 19 to 21 show the results of a series of experiments made using the adapted device.

In a first experiment with the adapted device of FIG. 14, a yeast solution was prepared by mixing 3 g of dried yeast with 4 g of granulated cane sugar and 100 ml warm water. The solution was placed into the device which was housed in an incubator set at 37° C. Reactance was measured over a seven hour period at 972 kHz. FIG. 19 shows the measured reactance values over the initial three hour period (except for a gap of ca. 15 minutes after 50 minutes had elapsed). The frequency employed is near to the resonant frequency of the electrical circuit comprising the device and the solution at the outset of measurements—this is clear from FIG. 19 because the reactance is initially close to zero. A large increase in the reactance is observed in the initial 25 minute period of measurement, followed by a plateau. The large increase in reactance can be attributed to a variation in the resonant frequency during this period. The reactance, when measured near resonance, is a sensitive indicator of changes in the resonant frequency because i) the reactance is zero at the resonant frequency, and ii) the gradient of the reactance verses frequency function is steep around the resonant frequency. Thus, large percentage changes in reactance are observed. Other quantities which vary sharply around the resonant frequency, such as dissipation factor and phase angle, are also likely to be sensitive indicators of variations of resonant frequency when measurements are made at spot frequencies near to resonance. It should be noted that resistance is much less suitable for this purpose.

In a second experiment with the adapted device of FIG. 14, 100 ml of fresh milk was placed into the device which was housed in an incubator set at 37° C.: Reactance was measured at 972 kHz over a period of 21 hours have elapsed. The initial reactance is close to zero, and rises to ca. 60 Ω over a period of ca 20 minutes, thereafter remaining approximately constant until four hours. FIG. 20 shows reactance over the period four to twenty-one hours, indicating that significant reductions in reactance are observed. The data imply that the resonant frequency is initially close to 972 kHz, and then, as the milk ages, the resonant frequency firstly drifts away from 972 kHz in the first twenty minutes and, secondly, slowly drifts back towards 972 kHz over a longer time period.

Figure 22:
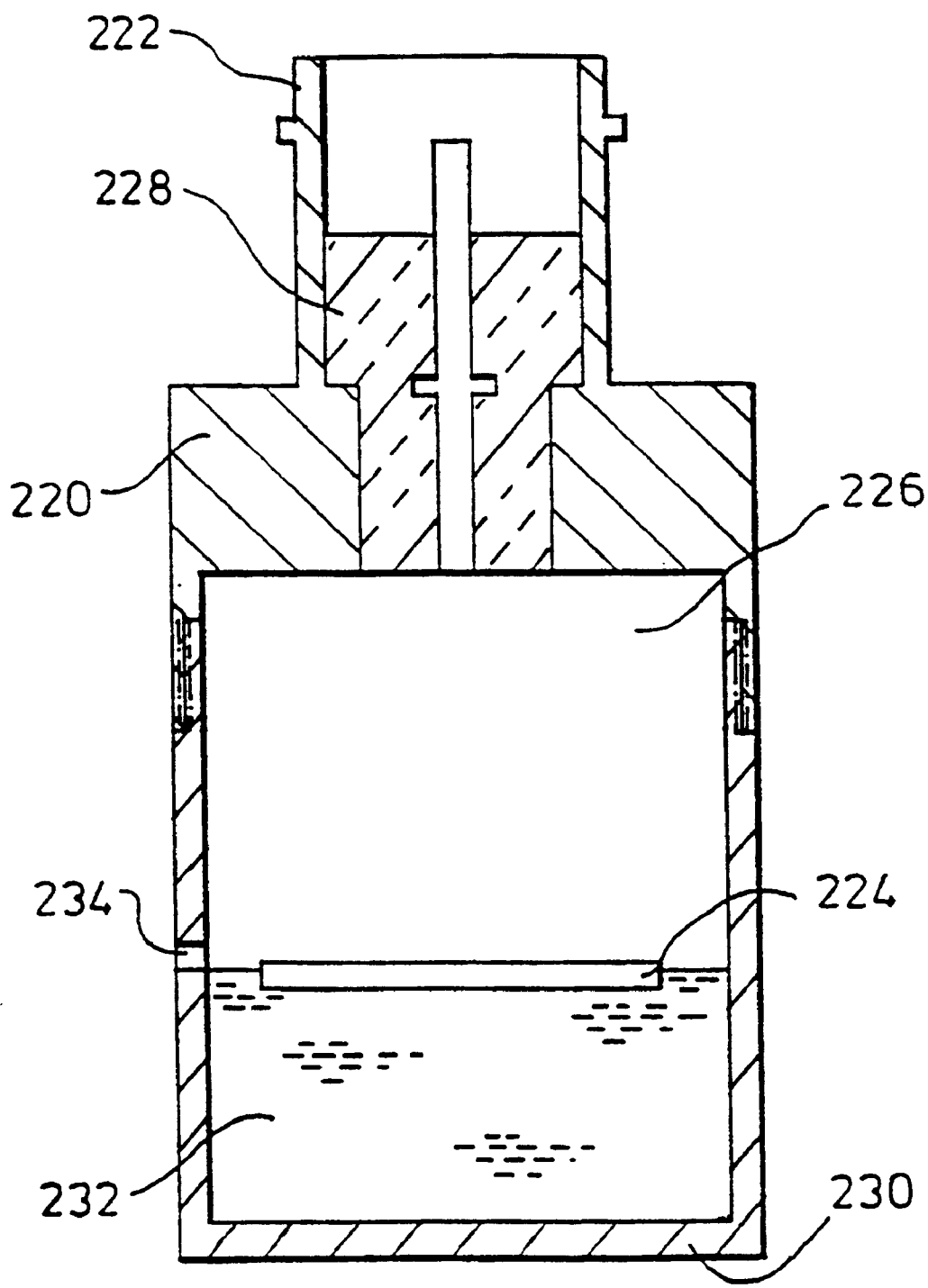
FIG. 22 shows the electrode arrangement of a fifth embodiment.

In a third experiment with the adapted device of FIG. 14, 100 ml samples of Coca-Cola (RTM), Pepsi-Cola (RTM), and a 50:50 mixture of the two were used. Dissipation factor was measured over the frequency range 972 to 974 kHz, the results being shown in FIG. 21. Excellent discrimination is observed between the dissipation factor functions of Coca-Cola (RTM) 210 and Pepsi-Cola (RTM) 212. Interestingly, the maximum of the dissipation factor function of the 50:50 mixture 214 does not lie between the maxima corresponding to the individual constituents, FIG. 22 shows a fifth embodiment of the invention suitable for impedance measurement of non-conductive liquids. The device comprises an upper portion 220 in threaded engagement with a lower portion 230. The upper portion 220 has an electrical connection 222 (BNC "baby N" connector) and cylindrical plate 224. The upper portion 220 also comprises a connector 226 allowing electrical connection to be made to the plate 224 via the connection 222, and an insulating piece 228. The lower portion 230 contains a sample 232 of non-conductive liquid and has an overflow outlet 234.

Figure 23:
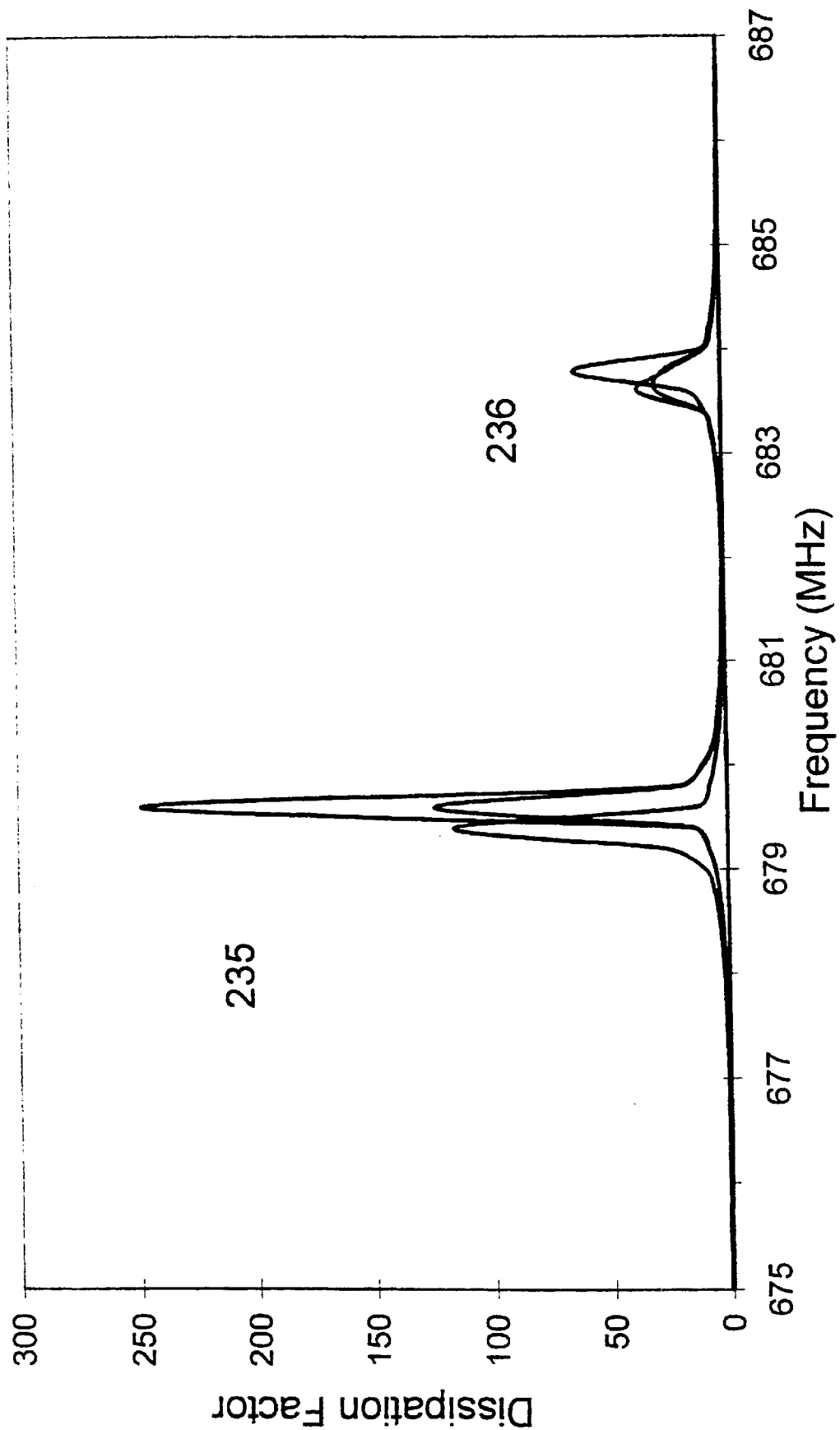
FIG. 23 shows dissipation factor for new and old samples of engine oil.

The device is connected to a Hewlett Packard 4191A RF impedance analyzer via a 4 cm coaxial cable. The resonant frequencies of the electrical circuit are relatively high since an inductor is not introduced into the circuit. Measurements of dissipation factor were made in the frequency range 675 to 687 MHz on two samples of an engine oil (Castrol GTX (RTM)). One sample was new, whilst the other had been used in an automobile for six months, in which time a distance of ca. 8,000 miles was travelled. FIG. 23 shows the results of a series of measurements of dissipation factor of both samples, and indicates that the maxima 235 associated with new oil are well separated from the maxima 236 associated with used oil. The former indicates a resonant frequency of 683.7 MHz whilst the latter indicate a resonant frequency of ca. 679.6 MHz. It should be noted that each sample of oil gives rise to a second resonant frequency around 450 MHz, and that these resonant frequencies may be detected in tandem to provide additional information.

Figure 24:
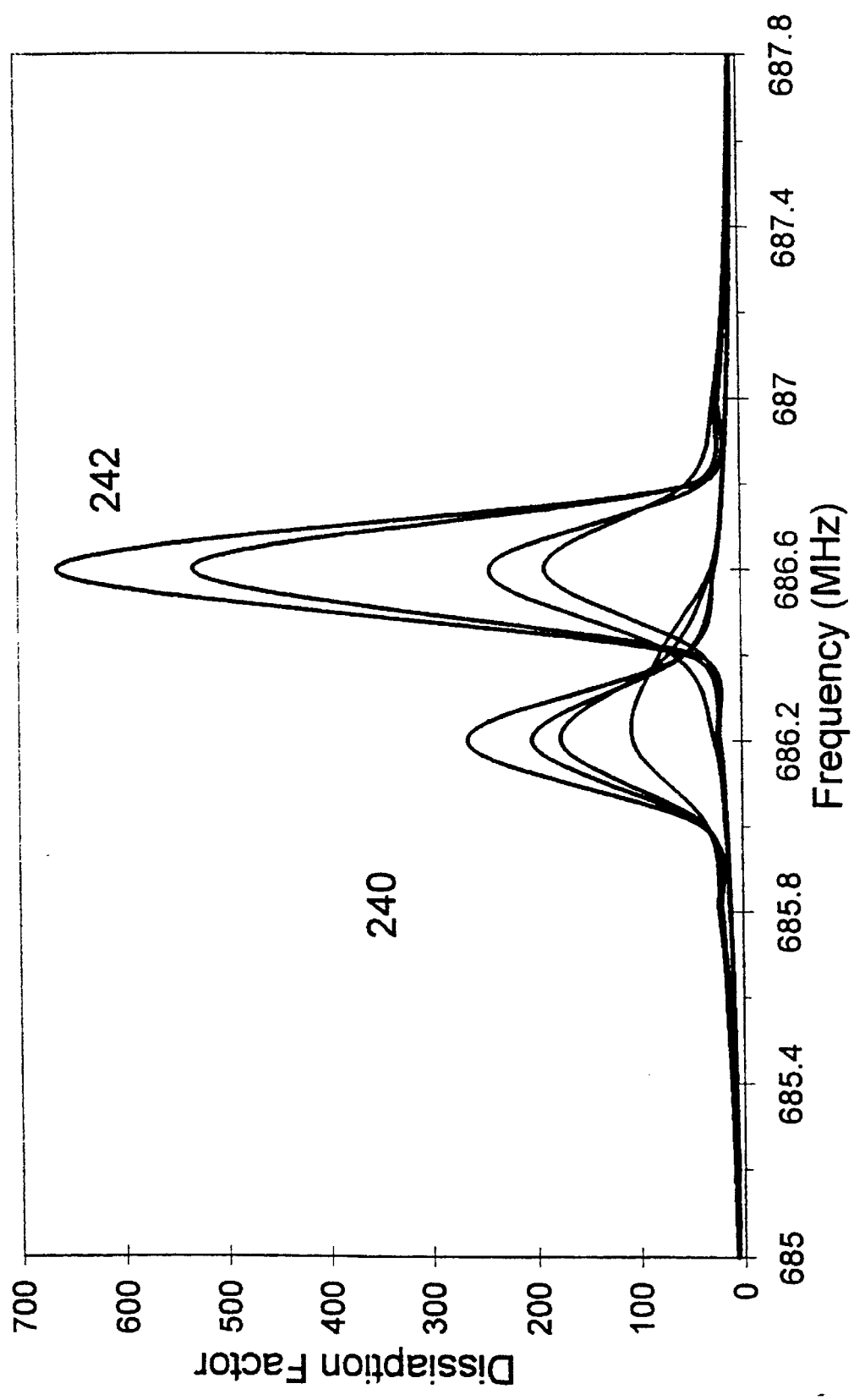
FIG. 24 shows dissipation factor for two sample of olive oil.

FIG. 24 shows dissipation factor measured in the frequency range 685 to 687.8 MHz using samples of two commercially available olive oils. A series of measurements were made on each sample. Maxima 240 associated with one type of olive oil are clustered around 686.2 MHz, whilst maxima 242 associated with the other type of olive oil are clustered around 686.6 Mhz.

It will be appreciated that further embodiments would suggest themselves to those skilled in the art which incorporate the general principle of utilising electrodes that are in some way protected from making direct electrical contact with the liquid. For example, a single coil may be disposed around the tubular member, and non-conductive materials other than glass may be employed. The third and fourth embodiments described above are well suited to the measurement of liquids flowing in pipes, particularly with regard to the on-line monitoring of drinking water quality. However, they are not limited in this regard, and might be adapted for use in rivers, lakes, storage tanks or other liquid sources.

It is advantageous that bio-fouling or corrosion of the electrodes themselves is eliminated. Furthermore, it is advantageous that the potential difference across the liquid itself is substantially less than the potential difference across the electrodes, since the possibility of inducing electrochemical reactions at high electrode potential differences is reduced.

It should be noted that the multi frequency measurement of impedance quantities is not restricted to the use of electrical signals. Further, electromagnetic signals may be used for this purpose. For example, microwave radiation of variable frequency may be directed to the liquid and an impedance quantity measured thereby. A primary example is the dissipation factor of the liquid, which can be derived from the reflected microwave power (presuming a knowledge of the microwave source output as a function of microwave frequency). The microwave source may be a tunable source, such as a Gunn diode. Alternatively, the use of a chirped microwave signal is within the scope of the invention. Other regions of the electromagnetic spectrum may be usefully employed.

The measurements of impedance quantities may be analysed in any appropriate manner, such as by comparison with a database or look up table of resonant frequency shifts. A preferred form of measurement analysis involves the use of artificial intelligence, for example, artificial neural networks; expert systems or fuzzy logic. A primary purpose of the present invention is on-line monitoring of water quality in flowing water systems such as rivers, industrial effluent, sewage flow or groundwater sources. As discussed previously, a problem with the on-line monitoring of the dc conductance of such systems is that changes in dc conductance might be caused by naturally occurring fluctuations in the composition of the water, rather than by the presence of pollutants. With the single experimental parameter provided by the dc conductance technique, it is difficult to differentiate between the two effects. With the present invention, the multiplicity of information provided by multifrequency measurements makes such differentiation a much more tractable problem. Nevertheless, it is to be anticipated that normally occurring variations in water composition will give rise to variations in the measured multifrequency impedance spectrum which will complicate the recognition of pollutants. The use of artificial intelligence, such as an artificial neural network, is advantageous in this regard because such systems can "learn" the normal variations in impedance and thus respond only to abnormal or unusual incidents. Alternatively, look up tables might incorporate the effects of such normally occurring variations.

Figure 17:
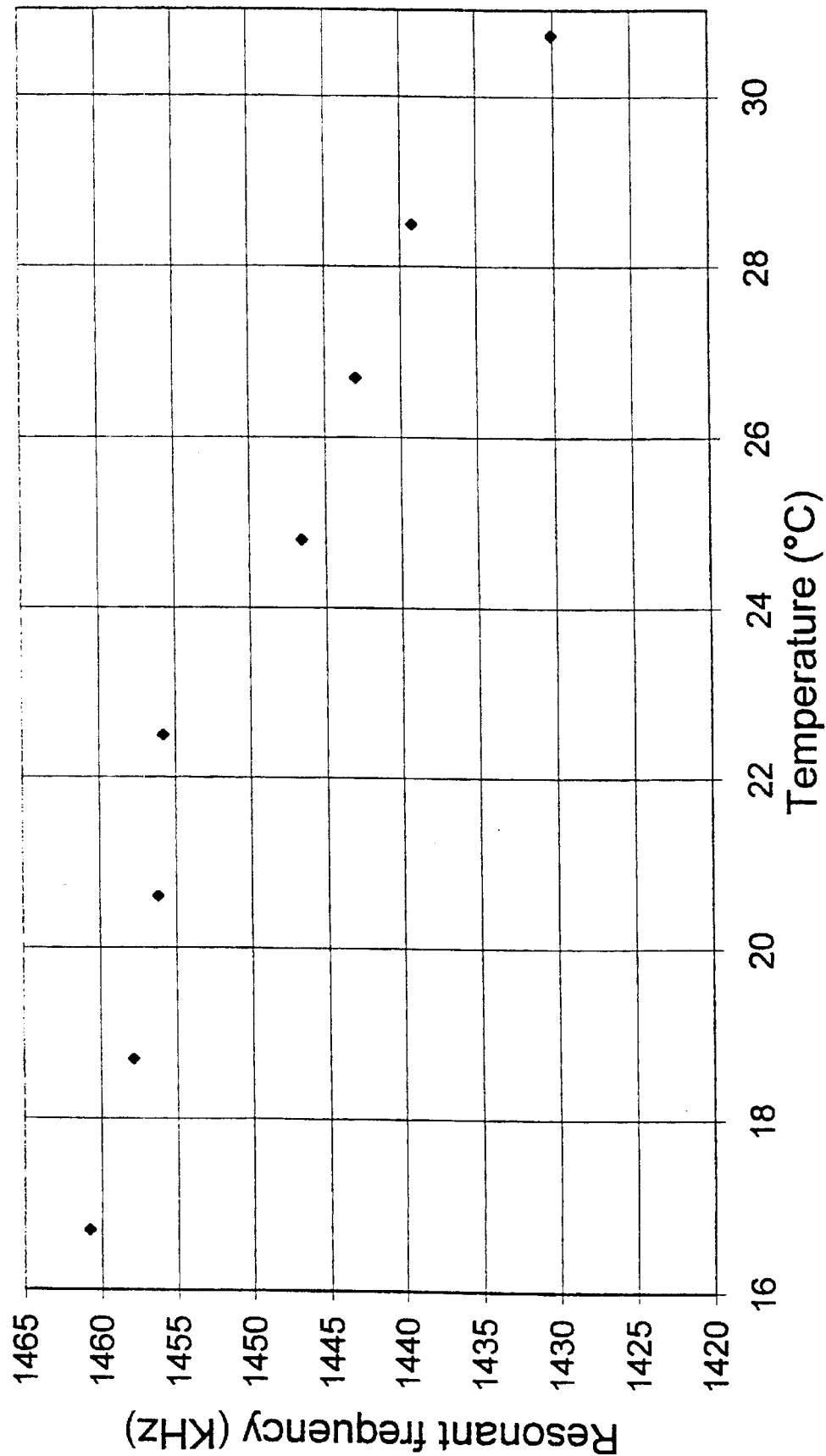
FIG. 17 shows the effect of temperature upon the resonant frequency of the first embodiment.
Figure 18:
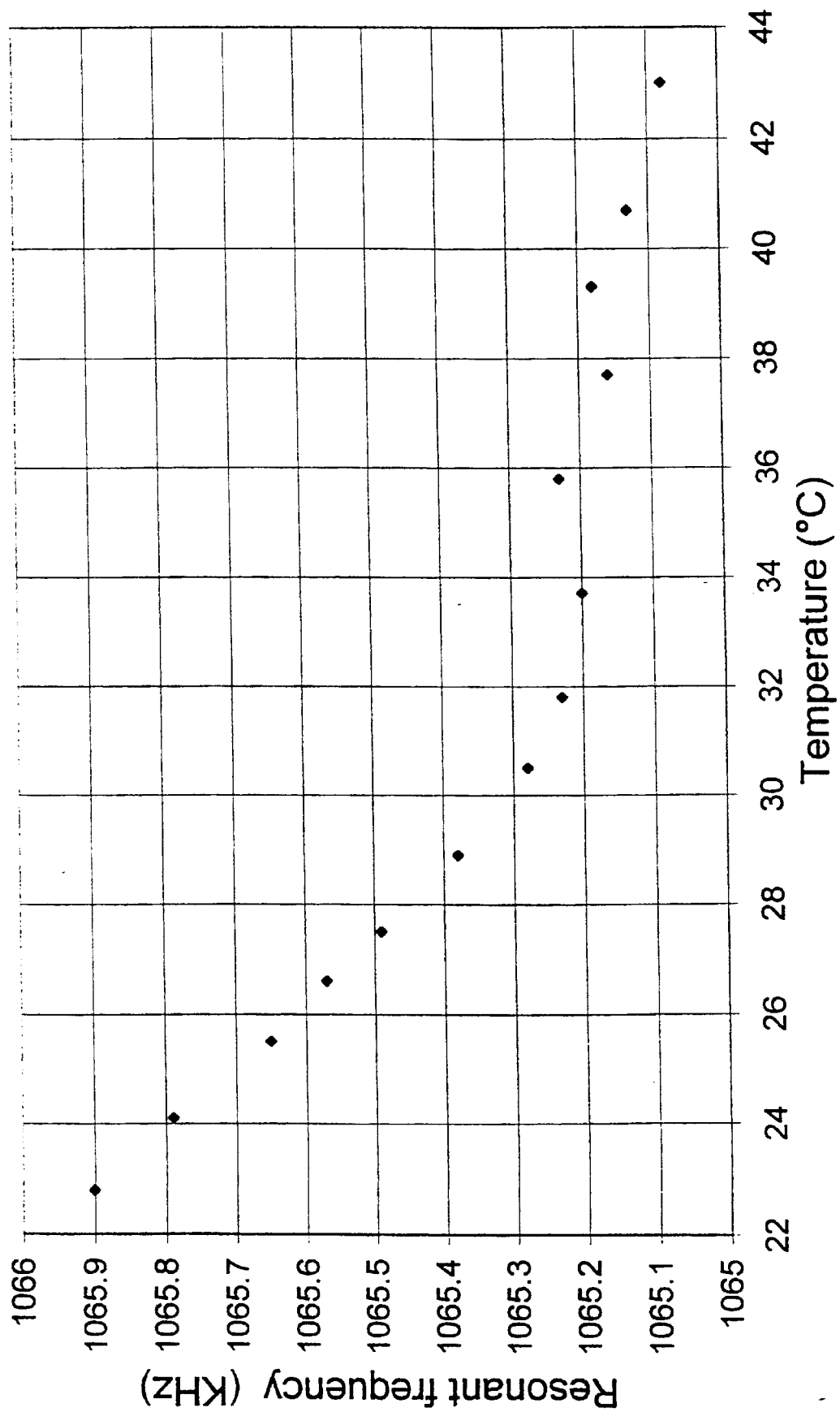
FIG. 18 shows the effect of temperature upon the resonant frequency of the fourth embodiment.

Numerous modifications to the above-described apparatus and method might be contemplated. For example, with the first embodiment, different electrode materials and configurations are possible. Furthermore, multiple electrode arrangements are within the scope of the invention. Modulation of the applied electric field strength is possible, in order to find the optimum working field strength or to provide additional information on the composition of the liquid. The use of high power ac fields, for example 10 V rms at 50 Hz, might alleviate the problem of bio-fouling of the electrodes. Water conductivity is temperature dependent, and this it is likely that account should be taken of temperature effects, particularly with in situ monitoring of "outdoors" water sources. One method is to train an artificial neural network to recognise variations caused by temperature. The temperature can, of course, be monitored, and this value can be used as an extra input to the neural network. Look up tables can be expanded to include the temperature dependence of the data. Another method is to incorporate an appropriate temperature conditioning system into the apparatus, for example a heated sample line. Another method still is to use an additional set of electrodes or windings as a "reference" system, measuring an impedance quantity of a known water standard such as a sample of de-ionised water. Thus, for example, resonant frequency shifts might be measured with respect to the resonant frequency measured in the standard, providing some compensation for the effects of any variations in ambient temperature on resonant frequency. Yet another method is to utilise a suitable temperature correction algorithm in the data analysis. FIGS. 17 and 18 show the effects of temperature on resonant frequency. The results shown in FIG. 17 were obtained using the first embodiment, whilst the results shown in FIG. 18 were obtained using the fourth embodiment. FIGS. 17 and 18 suggest that variations in the value of the resonant frequency caused by temperature may be corrected for using an appropriate algorithm which, at least over the temperature range from around room temperature up to 30° C., might comprise a simple linear relationship.

It is within the scope of the invention to provide a distributed system, in which measurements are made at a plurality of locations, and data relating to the measurements are relayed to a central location for data processing and/or analysis. The locations might be separated by quite considerable distances. A suitable telemetry system would be employed, such systems being known to one skilled in the art. Transmission of data by, for example, radio or microwave link, by cable or via telephone lines is within the scope of the invention.

It should be noted that the invention is not limited to the detection of pollutants per se in water: in fact, the form of the measured impedance spectrum is indicative of the composition of the sample. Thus, the present invention can be used more broadly as an analytical tool, or possibly in quality control or process control in, for example, the drinks industry. In fact, a range of beverages or liquid foodstuffs might be monitored. Processes such as brewing might be monitored. Additionally, the invention may be used to detect species deliberately introduced into a sample of water. Thus for example, an unknown substance may be dissolved or otherwise introduced into a sample of water and the technique of the present invention used to identify the unknown substance. The unknown substance may, in its normal state, be present as a gas, liquid or solid. In the case of a gas sample of unknown composition, it is clearly desirable that a suitable delivery systems is incorporated into the apparatus, so that the gas sample can be introduced to the sample of water in an air-tight manner. The impurity does not necessarily have to be dissolved in the water: a colloidal suspension, another liquid, or even particulate matter in the water may cause a change in the impedance of said water. For example, it is possible to detect air bubbles using the present invention, most conveniently by using a spot frequency electrical signal at or near to resonance, and observing changes in an impedance quantity such as reactance. The detection of air bubbles is important in a number of industrial process, and in medical applications, such as dialysis.

The invention can be used to detect microorganisms such as yeasts, fungi, bacteria and viruses.

As demonstrated earlier, it is not necessary that the liquid is highly conductive, since quantities related to the dielectric constant of the liquid can be monitored. Non-conductive liquids, such as oils can be monitored. Examples of oils include fatty oils, essential oils and mineral oils, such as petroleum products and lubricating oil compositions. The quality of the non-conductive liquid can be monitored in order to assess whether it has exceeded its working lifetime. Liquids used as components of a process might be interrogated in situ for this purpose. An example is the monitoring of engine oil quality in an automobile. Alternatively, the invention might be used for quality control of a product, such as a lubricating oil or a fuel. Quality might be assessed after or during poduction of the products, and the assessment might be integrated into a process control system, as described above.

What is claimed is:

1. A method for identifying a change in the composition of a liquid, comprising the steps of:
   applying a time varying electrical or electromagnetic input signal to the liquid in a range of frequencies encompassing a resonant frequency of an electrical circuit comprising the liquid;
   measuring an impedance quantity of the electrical circuit comprising the liquid by means of the output signal as a function of the frequency of the time varying electrical or electromagnetic input signal in said range of frequencies;
   determining a resonant frequency of the electrical circuit comprising the liquid;
   after a change in the composition of the liquid, measuring a variation in the impedance quantity at or near to the previously determined resonant frequency of the electrical circuit comprising the liquid; and
   relating the variation in the impedance quantity at or near to the resonant frequency of the electrical circuit comprising the liquid to a change in the composition of the liquid.

2. A method according to claim 1 in which the time varying electrical input signal is an ac input signal and the frequency of the ac input signal is varied.

3. A method according to claim 1 in which the step of measuring the impedance quantity comprises a time to frequency domain transformation on the output signal or on the combination of the input and output signal.

4. A method according to claim 1 in which the time varying input signal is periodic.

5. A method according to claim 1 wherein the electrical input signal is applied via one or more electrodes or windings which are not in direct electrical contact with the liquid.

6. A method according to claim 5 in which the one or more electrodes or windings are encased within a non-conductive material, and disposed in the liquid.

7. A method according to claim 1 in which an inductor is used to adjust the resonant frequency.

8. A method according to claim 1 in which the input signal is a microwave electromagnetic signal.

9. A method according to claim 1 further comprising the step of analysing the measurement of the impedance quantity with artificial intelligence means.

10. A method according to claim 9 in which the artificial intelligence means comprises an artificial neural network.

11. A method according to claim 1 comprising the step of analysing the measurement of the impedance quantity with reference to a look up table or algorithm based system.

12. A method according to claim 9 in which the step of analysing the measurement of the impedance quantity accounts for the effect of temperature on the measurement.

13. A method according to claim 1 in which the temperature of the liquid is controlled.

14. A method according to claim 1 in which the change in the composition of the liquid is caused by the presence of one or more impurities in the liquid.

15. A method according to claim 1 in which the liquid is water.

16. A method according to claim 1 in which measurements are made at a plurality of locations, and data relating to the measurements are relayed to a central location.

17. A method according to claim 1 in which the liquid is non-conducting.

18. A method according to claim 17 in which the liquid is oil.

19. A method according to claim 18 in which the quality of the oil is monitored.

20. A method according to claim 1 in which the change in composition of the liquid is caused by the presence of a microorganism in the liquid.

21. A method according to claim 1 in which the liquid is a beverage or a foodstuff.

22. Apparatus for assessing the composition of a liquid comprising:
    electrical signal applying means adapted to apply a time varying electrical signal to the liquid; and
    measuring means for measuring an impedance quantity at, or near to, the resonant frequency of an electrical circuit comprising the liquid so that the resonant frequency, or varitions in the resonant frequency, can be detected.

23. Apparatus according to claim 22 in which the electrical signal applying means applies an ac signal of variable frequency.

24. Apparatus according to claim 23 in which the measuring means comprises an impedance analyser.

25. Apparatus according to claim 22 in which the measuring means performs a time to frequency domain transformation of the time varying electrical signal.

26. Apparatus according to claim 25 in which the time varying electrical signal is periodic.

27. Apparatus according to claim 22 in which the electrical signal applying means is in direct electrical contact with the liquid.

28. Apparatus according to claim 27 in which the electrical signal applying means comprises at least two electrodes in direct electrical contact with the liquid.

29. Apparatus according to any of claims 22 to 26 in which the electrical signal applying means is not in direct electrical contact with the liquid.

30. Apparatus according to claim 29 in which a portion of the electrical signal applying means is encased within a non-conductive material, said portion being disposed in the liquid.

31. Apparatus according to claim 29 in which the electrical signal applying means are positioned around the liquid.

32. Apparatus according to claim 29 in which the electrical signal applying means comprises one or more electrodes.

33. Apparatus according to claim 29 in which the electrical signal applying means comprises at least two windings.

34. Apparatus according to claim 22 further comprising temperature control means adapted to maintain the liquid at a substantially constant temperature.

35. Apparatus according to claim 22 further comprising artificial intelligence means for analysing the measurement of an impedance quantity.

36. Apparatus according to claim 35 in which the artificial intelligence means is an artificial neural network.

37. A method as claimed in claim 1 wherein the time varying electrical input signal is a time varying electrical current.

38. The method according to claim 1 wherein the electrical circuit comprising the liquid is an open electrical circuit.

39. The method according to claim 1 wherein the electrical circuit comprising the liquid further comprises a container in which the liquid is contained and two electrodes.

40. The method according to claim 1 further comprising generating a time varying electrical or electromagnetic input signal in a closed oscillatory circuit.

* * * * *